US012697484B2

(12) United States Patent
Campean et al.

(10) Patent No.: US 12,697,484 B2
(45) Date of Patent: Aug. 4, 2026

(54) SYSTEM, METHOD, AND APPARATUS FOR APPLYING ELECTRICAL STIMULATION

(71) Applicant: AVATION MEDICAL, INC., Columbus, OH (US)

(72) Inventors: Alexandru Campean, Columbus, OH (US); Jeff A. Weisgarber, Columbus, OH (US); Mingming Zhang, Columbus, OH (US)

(73) Assignee: AVATION MEDICAL, INC., Columbus, OH (US)

( * ) Notice: Subject to any disclaimer, the term of this patent is extended or adjusted under 35 U.S.C. 154(b) by 462 days.

(21) Appl. No.: 17/760,806

(22) PCT Filed: Sep. 18, 2020

(86) PCT No.: PCT/US2020/051441
§ 371 (c)(1),
(2) Date: Mar. 16, 2022

(87) PCT Pub. No.: WO2021/055716
PCT Pub. Date: Mar. 25, 2021

(65) Prior Publication Data
US 2022/0347461 A1 Nov. 3, 2022

Related U.S. Application Data

(60) Provisional application No. 62/902,994, filed on Sep. 20, 2019.

(51) Int. Cl.
*A61N 1/04* (2006.01)
*A61N 1/36* (2006.01)

(52) U.S. Cl.
CPC ......... *A61N 1/0484* (2013.01); *A61N 1/0456* (2013.01); *A61N 1/36031* (2017.08); *A61N 1/36034* (2017.08)

(58) Field of Classification Search
None
See application file for complete search history.

(56) References Cited

U.S. PATENT DOCUMENTS 10,285,646 B1 * 5/2019 Grant .................... A61B 5/7221
2004/0093093 A1 5/2004 Andrews
(Continued)

FOREIGN PATENT DOCUMENTS

CN 202654544 U 1/2013
WO 2013071307 A1 5/2013
WO 2014003633 A1 1/2014

OTHER PUBLICATIONS

Australian Government Examination Report No. 2 for corresponding Application No. 2020348841, Applicant name: Avation Medical, Inc., dated Oct. 31, 2023; pp. 1-3.
(Continued)

*Primary Examiner* — Ankit D Tejani
(74) *Attorney, Agent, or Firm* — Tarolli, Sundheim, Covell & Tummino LLP

(57) ABSTRACT
A system, method, and apparatus for treating a medical condition by applying transcutaneous electrical stimulation to a target peripheral nerve of a subject. Electrical stimulation is applied to the peripheral nerve via a stimulation electrode pattern under closed-loop control in which EMG responses are monitored and used to adjust stimulation parameters. In response to detecting an unacceptable recording, electrical stimulation is applied to the peripheral nerve under open-loop control.

31 Claims, 19 Drawing Sheets

(56)                    References Cited

U.S. PATENT DOCUMENTS

| 2007/0265675 | A1 | 11/2007 | Lund et al. | |
|---|---|---|---|---|
| 2009/0018610 | A1 | 1/2009 | Gharib et al. | |
| 2014/0088394 | A1* | 3/2014 | Sunderland | A61B 5/254 |
| | | | | 600/373 |
| 2014/0142662 | A1 | 5/2014 | Yonce | |
| 2014/0148725 | A1 | 5/2014 | Cadwell | |
| 2015/0142082 | A1* | 5/2015 | Simon | A61N 1/36132 |
| | | | | 607/61 |
| 2016/0045747 | A1 | 2/2016 | Jiang et al. | |
| 2017/0266443 | A1* | 9/2017 | Rajguru | A61N 1/36034 |
| 2018/0043159 | A1 | 2/2018 | Hassan et al. | |
| 2018/0221672 | A1* | 8/2018 | Tranchina | A61N 1/3606 |
| 2019/0223764 | A1* | 7/2019 | Hulvershorn | A61N 1/0476 |

OTHER PUBLICATIONS

Australian Office Action—Examination Report No. 1 dated Sep. 12, 2023; Application No. 2022205207, Applicant name: Avation Medical, Inc., pp. 1-2.

PCT International Search Report for the corresponding International Application Serial No. PCT/US2020/051441, mailed Aug. 12, 2020, pp. 1-3.

First Canada Office Action, dated Jul. 26, 2023, corresponding to Application No. 3,151,721, PCT No. US2020051441, Owner Avation Medical Inc., pp. 1-3.

European Search Report for Corresponding Application Serial No. 22195414.2, Dated Jan. 1, 2023, pp. 1-7.

Corresponding European Patent Application No. 20785882.0, Communication Pursuant to Article 94(3) EPC, dated Jun. 4, 2025.

* cited by examiner

| Electrode | E1 | E2 | E3 | E4 | E5 | E6 | E7 | E8 |
|---|---|---|---|---|---|---|---|---|
| High Impedance? | N | N | N | N | N | Y | N | N |
| Pattern 1 | C |  | A | A |  |  |  |  |
| Pattern 2 |  | C | A | A |  |  |  |  |
| Pattern 3 | C | C |  |  | A | A |  |  |
| Pattern 4 | C | C | A |  |  |  |  |  |
| Pattern 5 | C | C |  | A |  |  |  |  |
| Pattern 6 |  |  |  |  | A | A |  | C |
| Pattern 7 |  |  | A | A | A | A | C |  |
| Pattern 8 |  |  |  |  |  |  | C | C |
| Pattern 9 |  |  |  |  |  | A | C | C |
| Pattern 10 |  |  |  |  | A |  | C | C |

400

600

620

610

600

620

610

600

610

620

620

600

610

600, 610

600, 610

600, 610

SYSTEM, METHOD, AND APPARATUS FOR APPLYING ELECTRICAL STIMULATION

RELATED APPLICATION

This application claims the benefit of U.S. Provisional Application Ser. No. 62/902,994, filed on Sep. 20, 2019, the subject matter of which is hereby incorporated by reference in its entirety.

TECHNICAL FIELD

The invention relates to electrical stimulation of peripheral nerves for the purpose of treating one or more medical conditions.

BACKGROUND

There are many known technologies that use electrical stimulation of peripheral nerves to treat medical conditions. Implantable stimulation technologies require surgical implantation of stimulation leads, with a pulse generator that is either surgically implanted or connected externally to wire leads. Percutaneous stimulation technologies are less invasive, but still require the stimulation electrodes to pierce the skin. Transcutaneous stimulation utilizes surface electrodes applied to a skin surface. Transcutaneous electrodes can, for example be mounted on pads that are applied to the skin by an adhesive. Other mounting structures, such as straps or braces, can also be used.

SUMMARY

According to one aspect, a system for applying electrical stimulation can be a transcutaneous electrical stimulation device that includes a wearable, such as a garment, sock, sleeve, brace, strap, etc. The wearable includes an electronic stimulator device that provides transcutaneous electrical stimulation to peripheral nerves for treatment of medical conditions. Advantageously, the wearable allows the subject to use the system at a time and place that is convenient. The subject may choose to use the device while they are at work or at home, or while walking, relaxing, or sleeping, as long as certain environments and/or activities (e.g., wet environments/activities) are avoided.

In this description, the system for applying transcutaneous stimulation is described as being used to treat a "subject," which is shown and described as being a human. The system for applying transcutaneous stimulation can, however, be used to treat non-human, i.e., animal, subjects, such as mammals.

Additionally, in this description, the system for applying electrical stimulation is described as a wearable device for applying transcutaneous electrical stimulation. While the structural characteristics of this device, i.e., the configurations of the strap/brace, electrode configuration/arrangement, controller, etc., illustrate some novel physical features of the system, other features, such as the stimulation control aspects of the system, can apply more broadly to other system configurations. For example, the control features/algorithms described herein, while shown and described in reference to being implemented in a transcutaneous stimulation systems, can also be implemented in percutaneous stimulation systems and implanted stimulation systems.

The wearable includes electrodes (i.e., two or more electrodes) that are arranged in a predetermined pattern or array, and that engage the subject's skin at desired locations when the wearable is worn. These skin surface mounted electrodes can, for example, be similar to those of other transcutaneous electrical nerve stimulation ("TENS") units to implement high voltage skin surface electrical stimulation. The electrodes include stimulating electrodes and recording electrodes, which the wearable can position at the same location or at different locations on the subject's skin. In fact, the identities of individual electrodes, i.e., stimulating or recording, can change depending on the application/treatment for which the system is being used. The stimulating electrodes apply the transcutaneous electrical stimulation to the subject's skin, and the recording electrodes record the electromyogram (EMG) responses elicited by the stimulation.

The wearable also includes a control unit that is electrically connected to the electrodes and that is operable to control electrical stimulation applied by the stimulating electrodes and to control the recording of EMG responses by the recording electrodes. The control unit executes closed-loop control algorithms, which adjust stimulation parameters, periodically or constantly, based on the elicited EMG response from the recruited nerves as feedback. Alternatively, instead of the EMG response providing the closed-loop feedback, or as a supplement to the EMG response, the system can include alternative devices, such as mechanomyogram (MMG) devices (e.g., an accelerometer), or can implement electronic measurements, such as electrode impedance, to implement the closed-loop control.

This closed-loop control can eliminate the need for "programming sessions" commonly required for neurostimulation systems. These sessions are necessitated by the variability in anatomical features, differences in neural or muscular response and the need for precise placement of the electrodes. To address this, and in order to find the arrangement that produces the desired response, the position of the electrodes can be adjusted and/or the size of the electrodes can be changed (e.g., enlarged). Additionally, the system can include multiple electrodes arranged in an array, and the system itself can select which electrodes to use. Any of these adjustments can be performed until an acceptable response (EMG and/or MMG) is achieved.

Once the electrodes are adjusted, the order, intensity, timing, etc. of the stimulation can be further tuned or adjusted to optimize the EMG and/or MMG response. The system can tailor the electrical stimulation applied by the electrodes so that the stimulation characteristics of each electrode (e.g., frequency, amplitude, pattern, duration, etc.) is configured to deliver the desired stimulation effect. This tailoring can be implemented automatically through the algorithm, which incrementally adjusts these characteristics, monitoring the and/or response at each increment until optimal settings are identified. Stimulation therapy can then be applied with these settings, according to the algorithm, which can be dictated by the requirements of the treating physician.

Throughout the electrical stimulation treatment process, the system can implement periodic or continuous measurement of system integrity. One such measurement is that of electrode impedance to remove the risks that can arise when electrodes lift away from the skin or certain properties of the electrodes or electronic circuitry deteriorate. The impedance measurement capability could also potentially be used to provide an indication of the optimal electrode location for nerve stimulation. This may be the case, for example, in areas where the skin is thin and where the stimulated nerves are most superficial. Thus, impedance values may be used as an input to the closed-loop stimulation algorithm to adjust stimulation parameters. By way of example, when stimulating the tibial nerve, the posterior area of the medial malleolus typically has comparatively thin skin and is the site where tibial nerve is most superficial, which leads to its being a good candidate for measuring electrode impedance.

The control unit and the architecture of the system may be designed to constantly optimize stimulation by monitoring the quality of nerve recruitment periodically or on a pulse-by-pulse basis, with the goal of keeping recruitment strength to a minimum (which can reduce muscle twitching) and to minimize the stimulation energy being delivered through the skin. The EMG recording feature is capable of detecting both M-wave and F-wave responses, which can be used as feedback inputs (together or independently) to the closed-loop stimulation algorithm to determine the level of activation of the stimulated peripheral nerve. A significant aspect of the F-wave is that it provides an indication that the stimulation-evoked peripheral nerve action potential has activated motor neurons in the associated spinal cord nerves/nerve plexus. For example, an F-wave response to tibial nerve stimulation indicates that the tibial nerve action potential has activated motor neurons in the sacral spinal cord/sacral plexus.

The wearable transcutaneous electrical stimulation device can be used to stimulate various peripheral nerves in order to improve medical conditions associated with those nerves. For instance, the system can be used to apply electrical stimulation to the tibial nerve, for example, to improve pelvic floor dysfunction as well as to improve pelvic floor function in healthy patients. Pelvic floor dysfunction includes bladder dysfunction and bowel dysfunction. Bladder dysfunction includes urinary incontinence such as urge incontinence, overactive bladder (OAB), mixed incontinence, and overflow incontinence. Bladder dysfunction also includes "voiding dysfunction," which refers to urinary incontinence, urinary retention conditions, high urinary frequency, high or low frequency of voiding, an underactive bladder, symptoms of bladder/pelvic pressure/pain, detrusor hyperreflexia, and voiding disorders caused by nerve damage, including interstitial cystitis. With respect to an underactive bladder, the system can be used to apply electrical stimulation to the tibial nerve, for example, to encourage the release of urine for patients with an underactive bladder. Regarding improving pelvic floor function in a healthy patient (i.e. those without an underlying pelvic floor disorder), the system can be used to apply electrical stimulation to the tibial nerve, for example, in order to temporarily decrease the urge to urinate. In such an aspect, a healthy patient can apply electrical stimulation voluntarily when the patient wants additional bladder control. Bowel dysfunction includes constipation (including idiopathic constipation), fecal incontinence, and problems with fecal movement, voiding and containment. Without wishing to be bound by theory, it is believed that tibial nerve stimulation can help to strengthen the pelvic floor muscles and sphincter complex to improve fecal incontinence. As such, improving pelvic floor dysfunction can also include modulating contraction of the pelvic floor or "pelvic diaphragm." Over time, therapy may cause contractions that restore the strength of pelvic organs and muscles, which may be a goal of the therapy. Stimulation induced modulation of the pelvic floor, sphincter or other targets can alleviate or eliminate many symptoms of urinary/fecal disorders.

The system also can be used to apply electrical stimulation to the tibial nerve, for example, to improve sexual dysfunction. Tibial nerve stimulation also can be used to improve genital arousal aspects of female sexual interest/arousal disorder by improving, for example, pelvic blood flow.

The system further can be used to apply electrical stimulation to the tibial nerve, for example, to improve plantar fasciitis.

The system also can be applied to the wrist area to provide stimulation to the ulnar nerve and/or median nerve, for example. The stimulation electrodes can, for example, be placed on the inside of the lower arm anywhere 0 to 20 cm from the wrist line. EMG recording electrodes can be placed on the base of thumb to record signal from the abductor/flexor pollicis brevis. EMG recording electrodes alternatively or additionally can be placed on the base of the fifth digit to record signal from the abductor/flexor digiti minimi brevis. The nerve activation can be confirmed by recording M-wave and F-wave EMG signals from the relevant muscles. The EMG signal can also be used as a control signal to adjust the stimulation parameters. This technology can be applied to median nerve activation, for example, for pain management in carpal tunnel syndrome, hypertension management, and nerve conduction study/nerve injury diagnosis for median/ulnar nerve neuropathy, etc.

The system also can be used to apply transcutaneous electrical stimulation to provide neurostimulation to peripheral nerves in order to enhance nerve regeneration after peripheral nerve injury. Furthermore, the system can be used to apply electrical stimulation to peripheral nerves to improve peripheral nerve pain.

Implementing closed-loop control, the system can utilize measured EMG responses to detect and obtain data related to the electrical activity of muscles in response to the applied stimulation. This data can be used as feedback to tailor the application of the electrical stimulation. Additionally or alternatively, the system can also implement MMG sensors, such as accelerometers, to measure the physical response of the muscles. Other feedback, such as impedance measurements between electrodes and other biopotential recording, can also be utilized. Through this closed-loop implementation, the system can utilize techniques such as current steering and nerve localization to provide peripheral nerve stimulation therapy for treating various medical conditions.

The system, method, and apparatus for applying transcutaneous electrical stimulation disclosed herein has many aspects, which can be included or utilized in various combinations.

According to one aspect, a method treats a medical condition by applying transcutaneous electrical stimulation to a target peripheral nerve of a subject.

According to another aspect, alone or in combination with any other aspect, the method can include positioning a plurality of stimulation electrodes on a skin surface proximate the targeted peripheral nerve, the stimulation electrodes being spaced from each other in a predetermined configuration. The method also can include positioning one or more recording electrodes on a skin surface remote from the stimulation electrodes at a location where electromyogram (EMG) responses to electrical stimulation of the targeted peripheral nerve can be detected. The method also can include stimulating the peripheral nerve by applying electrical stimulation pulses via the plurality of stimulation electrodes according to stimulation parameters under closed-loop control in which EMG responses to the electrical stimulation pulses are monitored via the recording electrodes and the stimulation parameters are adjusted in response to the monitored EMG responses. The method further can include, in response to detecting an unacceptable condition of the recording electrodes, applying electrical stimulation pulses via the stimulation electrode pattern according to the stimulation parameters under open-loop control in which the stimulation parameters are maintained without adjustment.

According to another aspect, alone or in combination with any other aspect, the unacceptable condition of the recording electrodes can include unacceptable impedance measurements.

According to another aspect, alone or in combination with any other aspect, the step of applying electrical stimulation pulses further can include monitoring for mechanomyogram (MMG) responses to the electrical stimulation pulses and applying the electrical stimulation pulses under closed-loop control in which the stimulation parameters are adjusted in response to the monitored MMG responses.

According to another aspect, alone or in combination with any other aspect, the step of applying electrical stimulation pulses can include detecting impedances of the recording electrodes and, in response to detecting acceptable impedances of the recording electrodes, applying the electrical stimulation pulses.

According to another aspect, alone or in combination with any other aspect, the method can include: obtaining sample measurements via the recording electrodes, checking the sample measurements for noise, checking the sample measurements for voluntary EMG responses, applying the electrical stimulation pulses under closed-loop control in response to determining an acceptable level of noise and the absence of voluntary EMG responses, and applying the electrical stimulation pulses under open-loop control in response to determining an unacceptable level of noise or the presence of voluntary EMG responses.

According to another aspect, alone or in combination with any other aspect, each application of an electrical stimulation pulse under closed-loop control can include: applying the electrical stimulation pulse, implementing a time delay, recording EMG responses via the recording electrodes after the time delay is executed, and adjusting the stimulation parameters in response to the recorded EMG responses. The duration of the time delay can be about 5 ms or less.

According to another aspect, alone or in combination with any other aspect, adjusting the stimulation parameters in response to the recorded EMG responses under closed loop control can include: increasing the amplitude and/or pulse width of subsequent stimulation pulses in response to the recorded EMG responses being below a predetermined EMG window, decreasing the amplitude and/or pulse width of subsequent stimulation pulses in response to the recorded EMG responses being above the predetermined EMG window, and maintaining the amplitude and/or pulse width of subsequent stimulation pulses in response to the recorded EMG responses being within the predetermined EMG window.

According to another aspect, alone or in combination with any other aspect, each application of an electrical stimulation pulse under open-loop control can include: applying the electrical stimulation pulse, and executing a time gap having a duration sufficient to maintain a constant stimulation period. The duration of the time gap can be 30-120 ms.

According to another aspect, alone or in combination with any other aspect, the stimulation electrodes can be arranged in an array and a pattern of stimulation electrodes can be selected from a pattern list, wherein the method further can further include generating the pattern list by:
    a) identifying a set of predetermined stimulation electrode patterns, each stimulation electrode pattern identifying which of the plurality of stimulation electrodes will apply the electrical stimulation pulses, and each stimulation electrode pattern having associated with it the stimulation parameters according to which it applies stimulation pulses;
    b) selecting a stimulation electrode pattern from the set of predetermined stimulation electrode patterns;
    c) generating a stimulation pulse using the selected stimulation electrode pattern according to its associated stimulation parameters;
    d) determining via the recording electrodes whether the stimulation pulse using the selected stimulation electrode pattern elicited an EMG response;
    e) adding the selected stimulation electrode pattern to the pattern list in response to detecting an EMG response;
    f) omitting the selected stimulation electrode pattern from the pattern list in response to not detecting an EMG response; and repeating steps b) through f) for each stimulation electrode pattern in the set of predetermined stimulation electrode patterns to complete the pattern list.

According to another aspect, alone or in combination with any other aspect, the method can include optimizing the stimulation electrode patterns in the pattern list by:
    g) adjusting the stimulation parameters for each stimulation electrode pattern in the pattern list to attempt to elicit an improved EMG response;
    h) selecting a stimulation electrode pattern from the set of predetermined stimulation electrode patterns;
    i) generating a stimulation pulse using the selected stimulation electrode pattern according to its associated stimulation parameters;
    j) determining via the recording electrodes whether the stimulation pulse using the selected stimulation electrode pattern elicited an EMG response;
    k) adding the selected stimulation electrode pattern to the pattern list in response to detecting an EMG response;
    l) omitting the selected stimulation electrode pattern from the pattern list in response to not detecting an EMG response; and repeating steps h) through l) for each stimulation electrode pattern in the set of predetermined stimulation electrode patterns to complete the pattern list. Steps h) through l) can be repeated until each electrode pattern in the pattern list is optimized.

According to another aspect, alone or in combination with any other aspect, the method can also include ordering the stimulation electrode patterns in the pattern list according to their elicited EMG and/or MMG responses.

According to another aspect, alone or in combination with any other aspect, stimulating the peripheral nerve can include stimulating the tibial nerve. Stimulating the peripheral nerve can include stimulating the tibial nerve at a location between the medial malleolus and the Achilles tendon.

According to another aspect, alone or in combination with any other aspect, monitoring EMG responses can include recording EMG signals that result from recruitment of the tibial nerve's motor fibers. This can include positioning the recording electrodes on the bottom of the subject's foot near the abductor hallucis and the flexor hallucis brevis to record the EMG signals.

According to another aspect, alone or in combination with any other aspect, stimulating the peripheral nerve can treat overactive bladder, sexual dysfunction, or plantar fasciitis.

According to another aspect, alone or in combination with any other aspect, stimulating the peripheral nerve can include stimulating the ulnar nerve and/or median nerve for pain management in carpal tunnel syndrome, hypertension management, and nerve conduction study/nerve injury diagnosis for median/ulnar nerve neuropathy, etc. Stimulating the ulnar nerve and/or median nerve can treat carpal tunnel syndrome or hypertension. Stimulating the ulnar nerve and/ or median nerve to perform a nerve conduction study or nerve injury diagnosis.

According to another aspect, alone or in combination with any other aspect, stimulating the ulnar nerve and/or median nerve can include positioning the stimulating electrodes on the inside of the lower arm 0 to 20 cm from the wrist line, and recording EMG responses can include positioning the recording electrodes on the base of thumb to record signal from abductor/flexor pollicis brevis, and/or positioning the recording electrodes on the base of pinky to record signal from abductor/flexor digiti minimi brevis.

According to another aspect, alone or in combination with any other aspect, stimulating the peripheral nerve can include applying the electrical stimulation pulses to the peripheral nerve to enhance nerve regeneration after peripheral nerve injury.

According to another aspect, alone or in combination with any other aspect, a system for treating overactive bladder by applying transcutaneous electrical stimulation to the tibial nerve of a subject can include a plurality of electrical stimulation electrodes, the stimulation electrodes being spaced from each other in a predetermined configuration, one or more recording electrodes, a structure for supporting the stimulation electrodes and the recording electrodes spaced apart from each other, and a control unit for controlling the operation of the stimulation electrodes and the recording electrodes. The control unit can be configured to perform the method according to any of the aspects disclosed herein, alone or in combination with any other aspect.

According to another aspect, alone or in combination with any other aspect, an apparatus for applying electrical stimulation includes a plurality of electrical stimulation electrodes spaced from each other in a predetermined configuration, one or more recording electrodes, a structure for supporting the stimulation electrodes and the recording electrodes spaced apart from each other, and a control unit for controlling the operation of the stimulation electrodes and the recording electrodes. The control unit is configured to energize the stimulation electrodes under closed-loop control using the recording electrodes to measure feedback, energize the stimulation electrodes under open-loop without measuring feedback, and determine whether to energize the stimulation electrodes under closed-loop control or open-loop control based on determining whether the feedback measured by the recording electrodes is reliable.

According to another aspect, alone or in combination with any other aspect, the structure can include a wearable structure configured to position the stimulation electrodes in the proximity of a peripheral nerve and to position the recording electrodes in the proximity of a muscle activated by the peripheral nerve.

According to another aspect, alone or in combination with any other aspect, the wearable structure can position the stimulation electrodes proximate the peripheral nerve and the recording electrodes proximate a location where EMG signals that result from recruitment of the peripheral nerve's motor fibers can be detected.

According to another aspect, alone or in combination with any other aspect, the wearable structure can include a strap, wherein the stimulation electrodes and recording electrodes are positioned at different locations along the length of the strap. The strap can be configured to have a portion wrapped around the subject's ankle to position the stimulating electrodes proximate the tibial nerve between the medial malleolus and the Achilles tendon. The strap can also be configured to have a portion wrapped around the subject's foot to position the recording electrodes on the bottom of the subject's foot near the abductor hallucis and the flexor hallucis brevis.

According to another aspect, alone or in combination with any other aspect, the wearable structure can include a brace comprising an upper portion upon which the stimulation electrodes are positioned and a lower portion upon which the recording electrodes are positioned. The upper portion of the brace can be configured to be wrapped around the subject's ankle to position the stimulating electrodes proximate the tibial nerve between the medial malleolus and the Achilles tendon. The lower portion of the brace can be configured to be wrapped around the subject's foot to position the recording electrodes on the bottom of the subject's foot near the abductor hallucis and the flexor hallucis brevis.

According to another aspect, alone or in combination with any other aspect, the apparatus can also include an accelerometer supported by the support structure adjacent or near the recording electrodes, wherein the control unit can be configured to determine whether to energize the stimulation electrodes under closed-loop control or open-loop control based on acceleration values determined by the accelerometer.

According to another aspect, alone or in combination with any other aspect, the control unit can include a microcontroller and a stimulator output stage controlled by the microcontroller. The stimulator output stage can include one or more channels for providing electrical current to the stimulating electrodes, wherein each channel of the output stage includes a current source and/or current sink, and wherein the output stage associated with each stimulating electrode determines whether the stimulating electrode operates as an anode or a cathode.

According to another aspect, alone or in combination with any other aspect, the microcontroller can be configured to determine amplitude and pulse width values for the current source and current sink for each channel of the output stage and their associated active stimulation electrodes.

According to another aspect, alone or in combination with any other aspect, the apparatus can include an impedance measurement circuit that is operatively connected to the stimulator output stage and is configured to measure electrode impedances.

According to another aspect, alone or in combination with any other aspect, the apparatus can include at least one analog input switch that is operatively connected to the microcontroller, wherein the microcontroller is configured to operate the analog input switch to determine which of the recording electrodes are used to measure feedback.

According to another aspect, alone or in combination with any other aspect, the apparatus can include an analog front end circuit that is operatively connected to the analog input switch, wherein the analog front end is configured to facilitate sampling the recording electrodes at a predetermined sample rate in order to determine whether the feedback measured by the recording electrodes is reliable. The sample rate can be 1,000-8,000 samples per second or more, for example, up to 20,000 samples per second.

According to another aspect, alone or in combination with any other aspect, the microcontroller can be configured to initiate via the analog front end a sampling window after energizing the stimulation electrodes, wherein during the sampling window the recording electrodes are used to measure feedback signals to determine whether EMG data is present.

According to another aspect, alone or in combination with any other aspect, the apparatus can include a radio for communicating wirelessly with an external device for programming the microcontroller, uploading/downloading data, and remotely monitoring and/or controlling operation of the control unit.

According to another aspect, alone or in combination with any other aspect, a method for treating overactive bladder can include applying transcutaneous electrical stimulation to the tibial nerve of a subject. The method can include positioning a plurality of stimulation electrodes on a skin surface at a location between the medial malleolus and the Achilles tendon proximate the tibial nerve, the stimulation electrodes being spaced from each other in a predetermined configuration. The method also can include positioning one or more recording electrodes on a skin surface remote from the stimulation electrodes at a location on the bottom of the subject's foot near the abductor hallucis and the flexor hallucis brevis muscles to record electromyogram (EMG) responses that result from recruitment of the tibial nerve's motor fibers. The method also can include stimulating the tibial nerve by applying electrical stimulation pulses via a stimulation electrode pattern selected from the plurality of stimulation electrodes according to stimulation parameters under closed-loop control in which EMG responses to the electrical stimulation pulses are monitored via the recording electrodes and the stimulation parameters are adjusted in response to the monitored EMG responses. The method further can include, in response to detecting an unacceptable condition of the recording electrodes, applying electrical stimulation pulses via the stimulation electrode pattern according to the stimulation parameters under open-loop control in which the stimulation parameters are maintained without adjustment.

According to another aspect, alone or in combination with any other aspect, a system for treating overactive bladder by applying transcutaneous electrical stimulation to the tibial nerve of a subject can include a plurality of electrical stimulation electrodes, the stimulation electrodes being spaced from each other in a predetermined configuration, one or more recording electrodes, a structure for supporting the stimulation electrodes and the recording electrodes spaced apart from each other, and a control unit for controlling the operation of the stimulation electrodes and the recording electrodes. The control unit can be configured to perform the method according to any of the aspects disclosed herein, alone or in combination with any other aspect.

According to another aspect, a method for treating a medical condition by delivering electrical stimulation to a target peripheral nerve of a subject includes positioning a plurality of stimulation electrodes in a predetermined configuration proximate the target peripheral nerve. The method also includes positioning one or more recording electrodes remote from the stimulation electrodes at a location where electromyogram (EMG) responses to electrical stimulation of the target peripheral nerve can be detected. The method also includes localizing the target peripheral nerve by applying electrical stimulation pulses to the target peripheral nerve via the plurality of stimulation electrodes with different stimulation energies, monitoring via the recording electrodes the EMG responses elicited by each electrical stimulation pulse, and identifying pulse energies that elicit an acceptable activation of the target peripheral nerve. The method also includes, in response to identifying pulse energies that elicit an acceptable activation of the target peripheral nerve, initially delivering stimulation to the target peripheral nerve by applying electrical stimulation pulses via the electrodes at the identified pulse energies that elicited the acceptable activation of the target peripheral nerve. The method further includes thereafter delivering electrical stimulation to the target peripheral nerve to treat the medical condition by controlling the delivery of stimulation to the target peripheral nerve using closed-loop control in which EMG responses to the electrical stimulation pulses are monitored via the recording electrodes and stimulation parameters are adjusted in response to the monitored EMG responses.

According to another aspect, alone or in combination with other aspects, the stimulation parameters can include at least one of an amplitude of the electrical stimulation pulses, a modulation pattern of the electrical stimulation pulses, the frequency of the electrical stimulation pulses, the duration of the electrical stimulation pulses, and the polarity of the stimulation electrodes.

According to another aspect, alone or in combination with other aspects, controlling the delivery of stimulation to the target peripheral nerve using closed-loop control can include: obtaining EMG measurements via the recording electrodes, checking the EMG measurements for at least one of noise and voluntary EMG responses, and applying the electrical stimulation pulses under closed-loop control in response to determining an acceptable level of noise and/or the absence of voluntary EMG responses.

According to another aspect, alone or in combination with other aspects, controlling the delivery of stimulation to the target peripheral nerve using closed-loop control can include: applying the electrical stimulation pulse, implementing a time delay, recording EMG responses via the recording electrodes after the time delay, and adjusting the stimulation parameters in response to the recorded EMG responses. According to this aspect, the duration of the time delay can be about 5 ms or less.

According to another aspect, alone or in combination with other aspects, adjusting the stimulation parameters in response to the recorded EMG responses under closed loop control can include: adjusting the stimulation parameters of subsequent stimulation pulses in response to the recorded EMG responses being outside a predetermined EMG window, and maintaining the stimulation parameters of subsequent stimulation pulses in response to the recorded EMG responses being within the predetermined EMG window.

According to another aspect, alone or in combination with other aspects, adjusting the stimulation parameters in response to the recorded EMG responses under closed loop control can include: increasing the output of subsequent stimulation pulses in response to the recorded EMG responses being below a predetermined EMG window, decreasing the output of subsequent stimulation pulses in response to the recorded EMG responses being above the predetermined EMG window, and maintaining the output of subsequent stimulation pulses in response to the recorded EMG responses being within the predetermined EMG window.

According to another aspect, alone or in combination with other aspects, the method can also include: detecting an unacceptable condition of the recording electrodes in response to failing to elicit an acceptable activation of the target peripheral nerve during the localizing step and, in response to detecting the unacceptable condition of the recording electrodes, controlling the delivery of stimulation to the target peripheral nerve using open-loop control in which stimulation is delivered to the target peripheral nerve using stimulation parameters are applied without regard to the monitored EMG responses.

According to another aspect, alone or in combination with other aspects, each application of an electrical stimulation pulse under open-loop control can include: applying the electrical stimulation pulse, and executing a time gap having a duration sufficient to maintain a constant stimulation period. According to this aspect, the duration of the time gap can be about 75 ms.

According to another aspect, alone or in combination with other aspects, the unacceptable condition of the recording electrodes can include at least one of an unacceptable impedance measurement, an unacceptable noise measurement, or the detection of a voluntary EMG response.

According to another aspect, alone or in combination with other aspects, the nerve localization step can include: obtaining sample measurements via the recording electrodes, checking the impedance of the recording electrodes, checking the sample measurements for at least one of noise and voluntary EMG responses, controlling the delivery of stimulation to the target peripheral nerve using closed-loop control in response to determining an acceptable recording electrode impedance and an acceptable level of noise and/or the absence of voluntary EMG responses, and controlling the delivery of stimulation to the target peripheral nerve using open-loop control in response to determining an unacceptable recording electrode impedance, an unacceptable level of noise, or the presence of voluntary EMG responses.

According to another aspect, alone or in combination with other aspects, the plurality of stimulation electrodes can include three or more stimulation electrodes. According to this aspect, localizing the target peripheral nerve can include: applying electrical stimulation pulses to the target peripheral nerve via different combinations of the plurality of stimulation electrodes with different stimulation energies, monitoring via the recording electrodes the EMG responses elicited by each electrical stimulation pulse, and identifying both the stimulation electrode combinations and the pulse energies that elicit an acceptable activation of the target peripheral nerve. According to this aspect, initially delivering stimulation to the target peripheral nerve can include applying electrical stimulation pulses via the identified combinations of stimulation electrodes at the identified pulse energies that elicited the acceptable activation of the target peripheral nerve. This aspect can also include delivering electrical stimulation to the target peripheral nerve to treat the medical condition by controlling the delivery of stimulation to the target peripheral nerve using closed-loop control comprises delivering electrical stimulation via the identified combinations of stimulation electrodes.

According to another aspect, alone or in combination with other aspects, stimulating the peripheral nerve can include stimulating the tibial nerve, and wherein monitoring the EMG responses via the recording electrodes comprises recording EMG signals that result from recruitment of the tibial nerve's motor fibers.

According to another aspect, alone or in combination with other aspects, positioning a plurality of stimulation electrodes can include positioning the plurality of stimulation electrodes at a location between the medial malleolus and the Achilles tendon. Positioning one or more recording electrodes can include positioning the one or more recording electrodes on the bottom of the subject's foot near the abductor hallucis and the flexor hallucis brevis.

According to another aspect, alone or in combination with other aspects, the medical condition can include pelvic floor dysfunction.

According to another aspect, alone or in combination with other aspects, the medical condition can include bladder dysfunction.

According to another aspect, alone or in combination with other aspects, the medical condition can include urinary incontinence, which can include at least one of urge incontinence, overactive bladder (OAB), mixed incontinence, and overflow incontinence.

According to another aspect, alone or in combination with other aspects, the medical condition can include voiding dysfunction, which can include at least one of urinary incontinence, urinary retention conditions, high urinary frequency, high frequency of voiding, low frequency of voiding, underactive bladder, symptoms of bladder/pelvic pressure/pain, detrusor hyperreflexia, and voiding disorders caused by nerve damage, including interstitial cystitis.

According to another aspect, alone or in combination with other aspects, the medical condition can include bowel dysfunction.

According to another aspect, alone or in combination with other aspects, the medical condition can include constipation, idiopathic constipation, fecal incontinence, problems with fecal movement, problems with fecal voiding, and problems with fecal containment.

According to another aspect, alone or in combination with other aspects, the medical condition can include improving pelvic floor function bowel dysfunction.

According to another aspect, alone or in combination with other aspects, delivering electrical stimulation to the target peripheral nerve to treat the medical condition can include stimulating the ulnar nerve and/or median nerve for pain management in carpal tunnel syndrome, hypertension management, and nerve conduction study/nerve injury diagnosis for median/ulnar nerve neuropathy.

According to another aspect, alone or in combination with other aspects, delivering electrical stimulation to the target peripheral nerve to treat the medical condition can include stimulating the ulnar nerve and/or median nerve to treat carpal tunnel syndrome or hypertension.

According to another aspect, alone or in combination with other aspects, delivering electrical stimulation to the target peripheral nerve to treat the medical condition can include stimulating the ulnar nerve and/or median nerve to perform a nerve conduction study or nerve injury diagnosis.

According to another aspect, alone or in combination with other aspects, delivering electrical stimulation to the target peripheral nerve to treat the medical condition can include applying the electrical stimulation pulses to the peripheral nerve to enhance nerve regeneration after peripheral nerve injury.

According to another aspect, alone or in combination with other aspects, delivering electrical stimulation to the target peripheral nerve to treat the medical condition can include applying the electrical stimulation pulses to the peripheral nerve to treat pelvic pain.

According to another aspect, alone or in combination with other aspects, delivering electrical stimulation to the target peripheral nerve to treat the medical condition can include applying the electrical stimulation pulses to the peripheral nerve to treat peripheral neuropathy.

According to another aspect, alone or in combination with other aspects, a system for treating a medical condition by applying electrical stimulation to a target peripheral nerve of a subject, can include a plurality of electrical stimulation electrodes, one or more recording electrodes, and a control unit for controlling the operation of the stimulation electrodes and the recording electrodes according to the methods according to any of the aforementioned aspects.

According to another aspect, alone or in combination with other aspects, a controller can control the operation of a plurality of electrical stimulation electrodes and one or more recording electrodes to treat a medical condition by applying electrical stimulation to a target peripheral nerve of a subject according to the methods according to any of the aforementioned aspects.

DRAWINGS

Figure 1A:
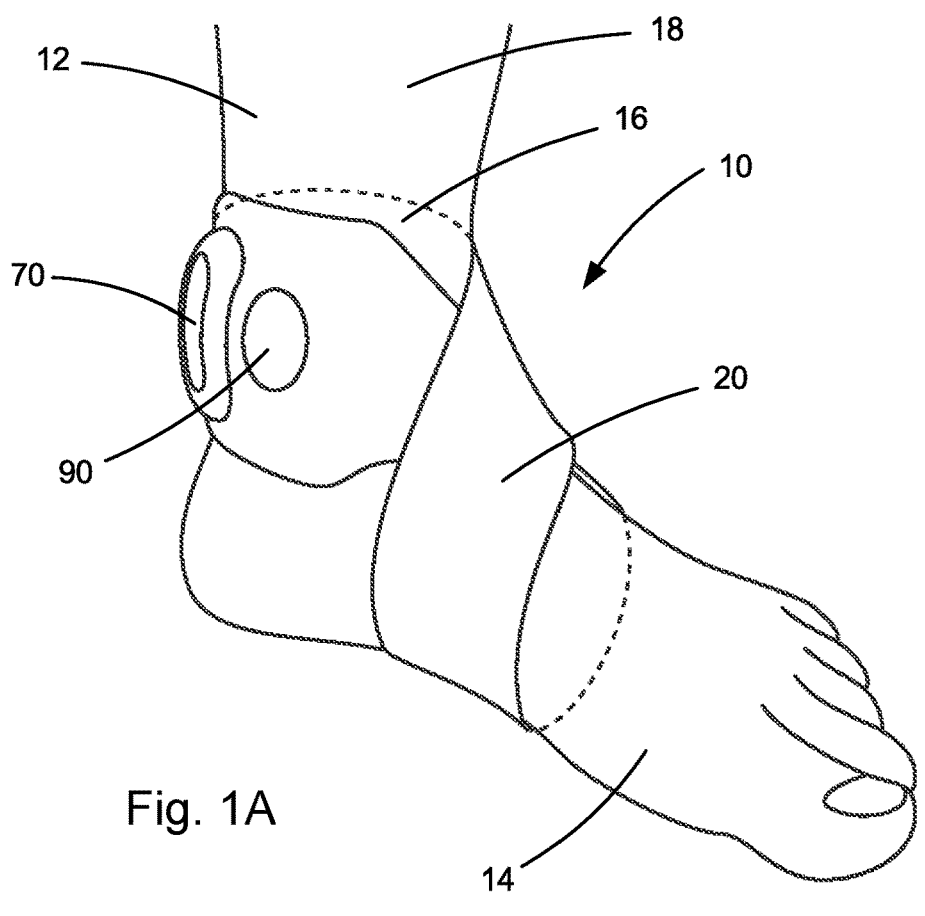
FIG. 1A illustrates a left-foot implementation of an electronic medical device for delivering transcutaneous electrical stimulation of peripheral nerves, according to a first example configuration.
Figure 1B:
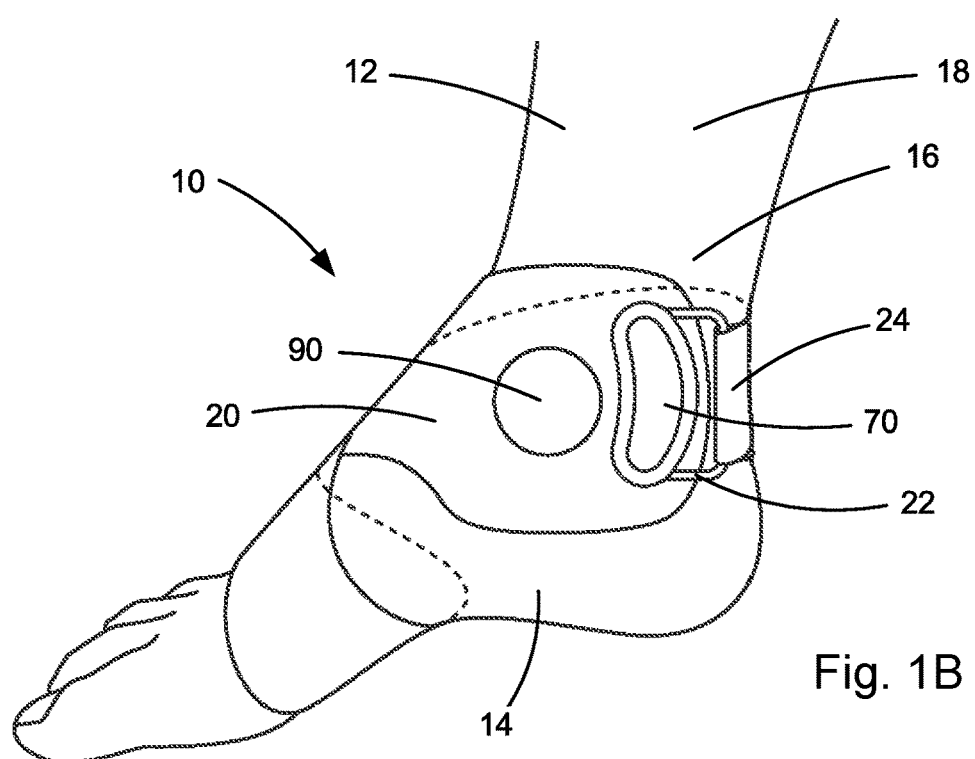
FIG. 1B illustrates a right-foot implementation of the electronic medical device for delivering transcutaneous electrical stimulation of peripheral nerves, according to the first example configuration.
Figures 2A, 2B:
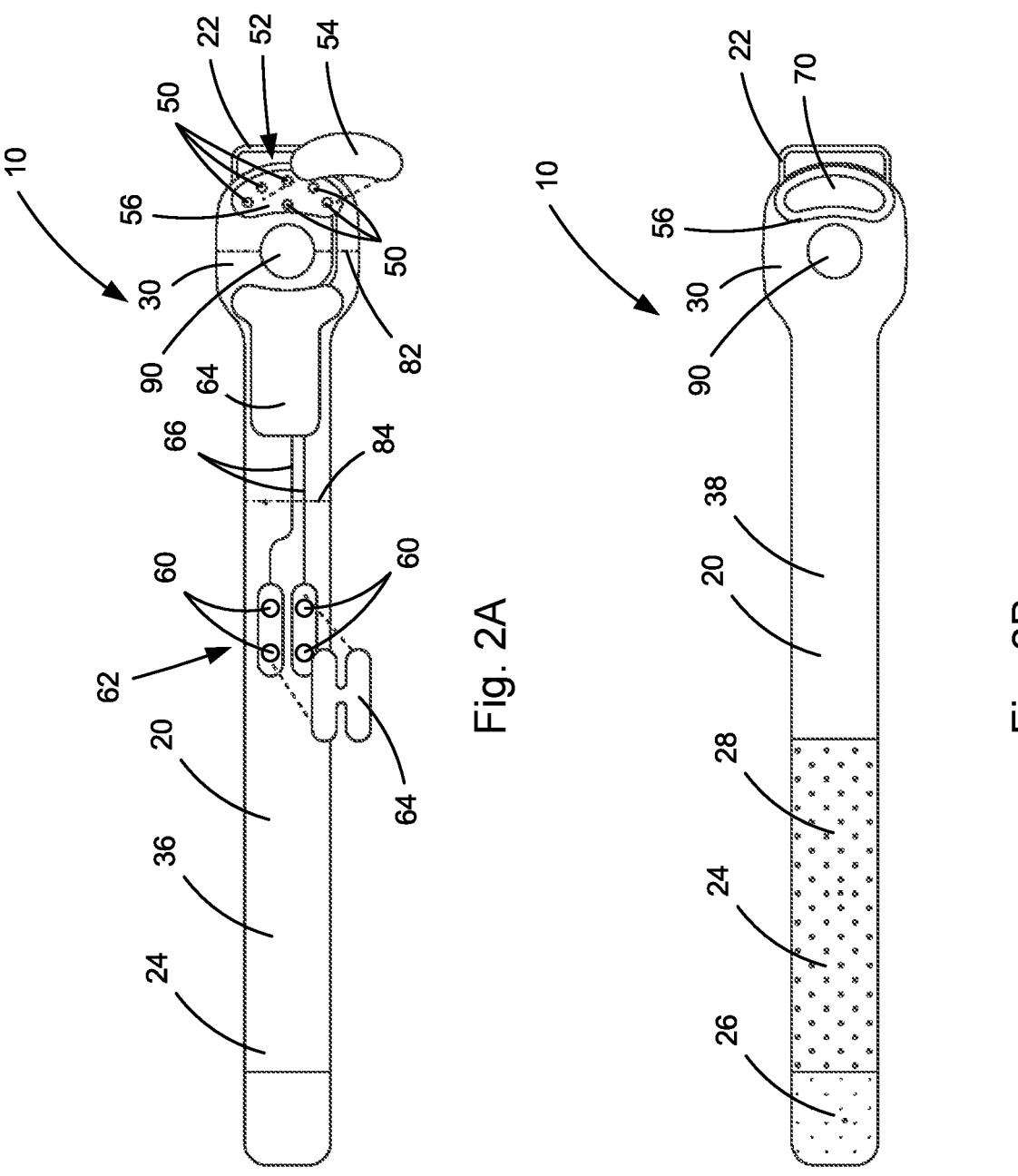
FIG. 2A is an inner surface plan view of the electronic medical device of FIGS. 1A and 1B.
FIG. 2B is an outer surface plan view of the electronic medical device of FIGS. 1A and 1B.
Figures 2C, 2D, 2E:
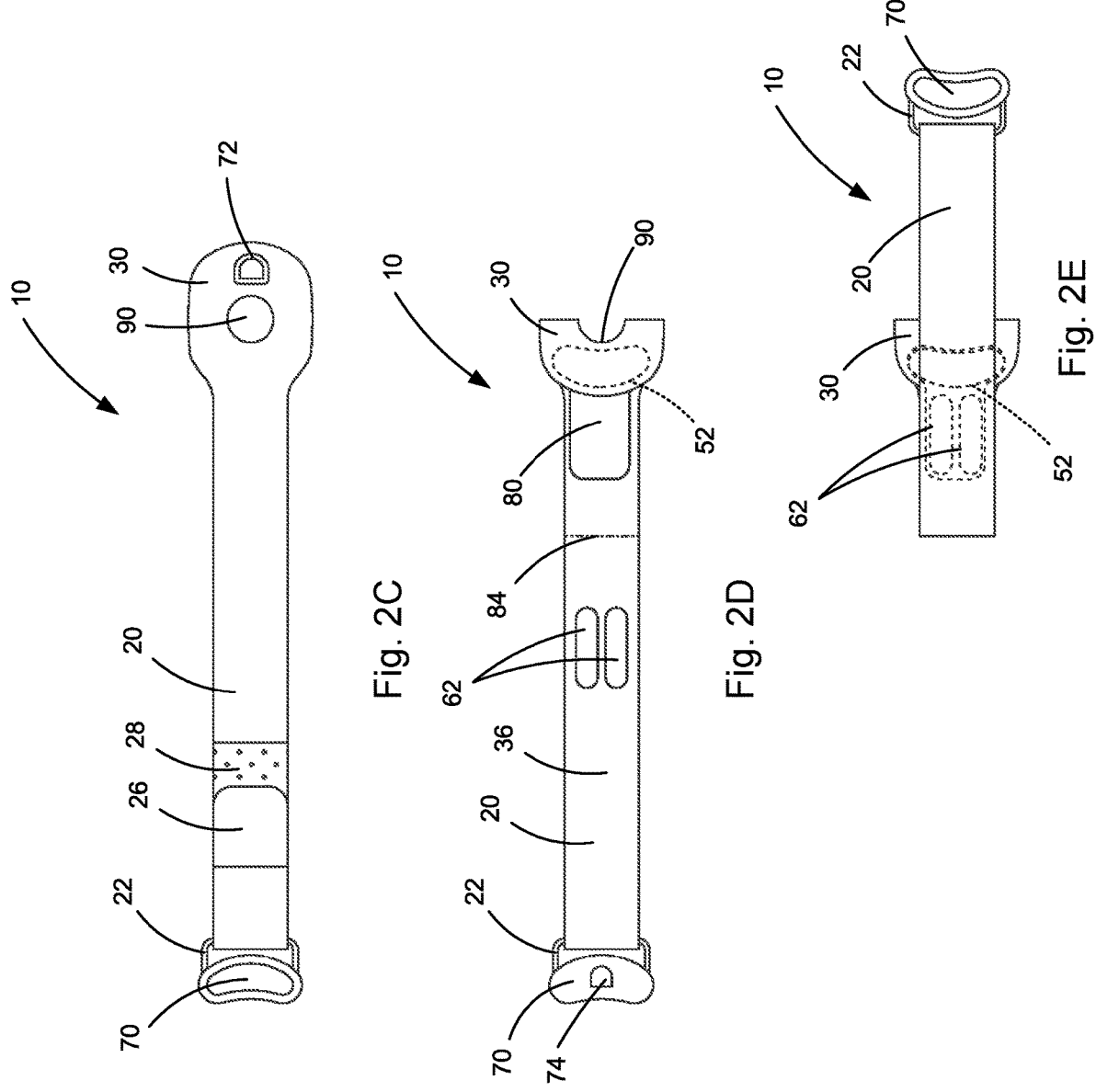

FIGS. 2C-E are outer surface plan views of the electronic medical device of FIGS. 1A and 1B illustrating sequential steps in preparing the device for use.

Figure 3A:
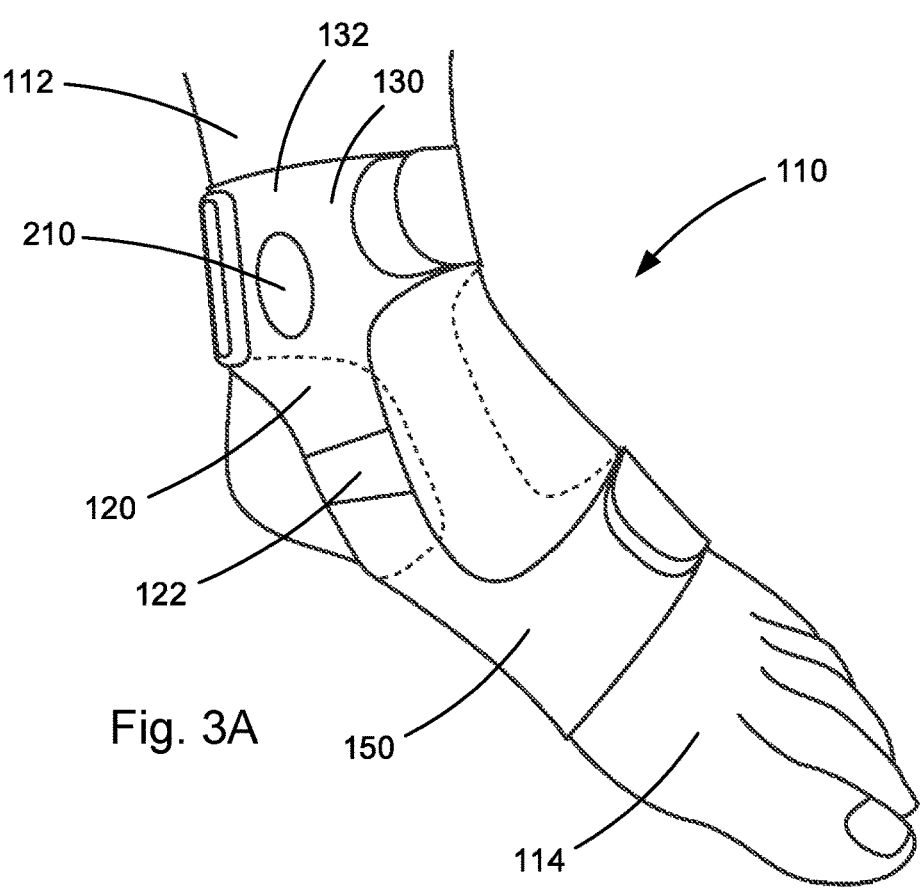

FIG. 3A illustrates a left-foot implementation of an electronic medical device for delivering transcutaneous electrical stimulation of peripheral nerves, according to a second example configuration.

Figure 3B:
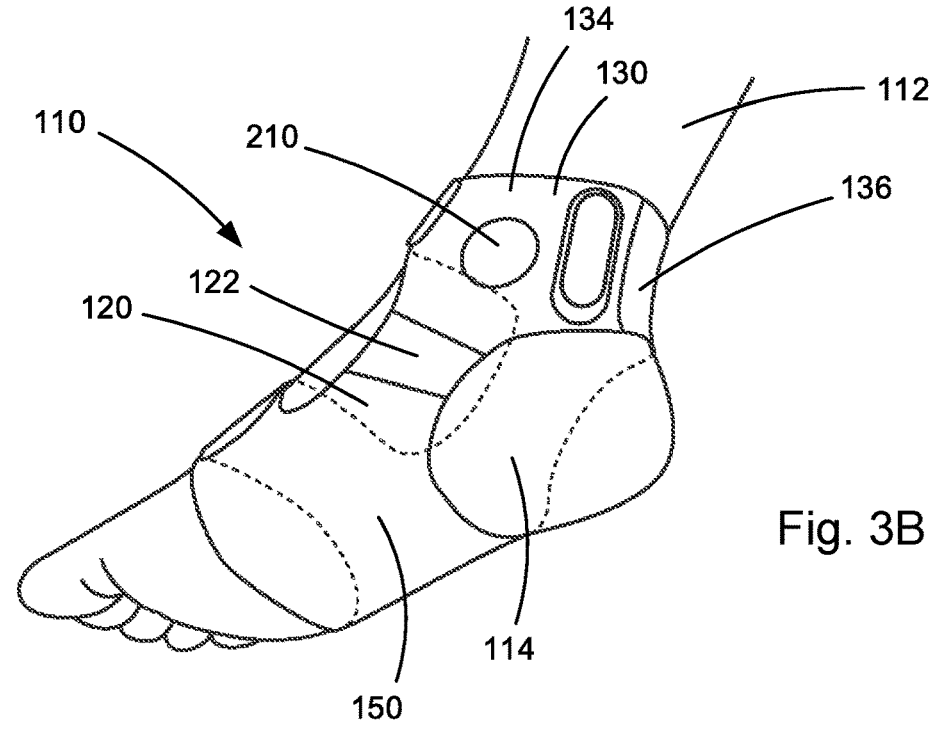

FIG. 3B illustrates a right-foot implementation of the electronic medical device for delivering transcutaneous electrical stimulation of peripheral nerves, according to the second example configuration.

Figure 4A:
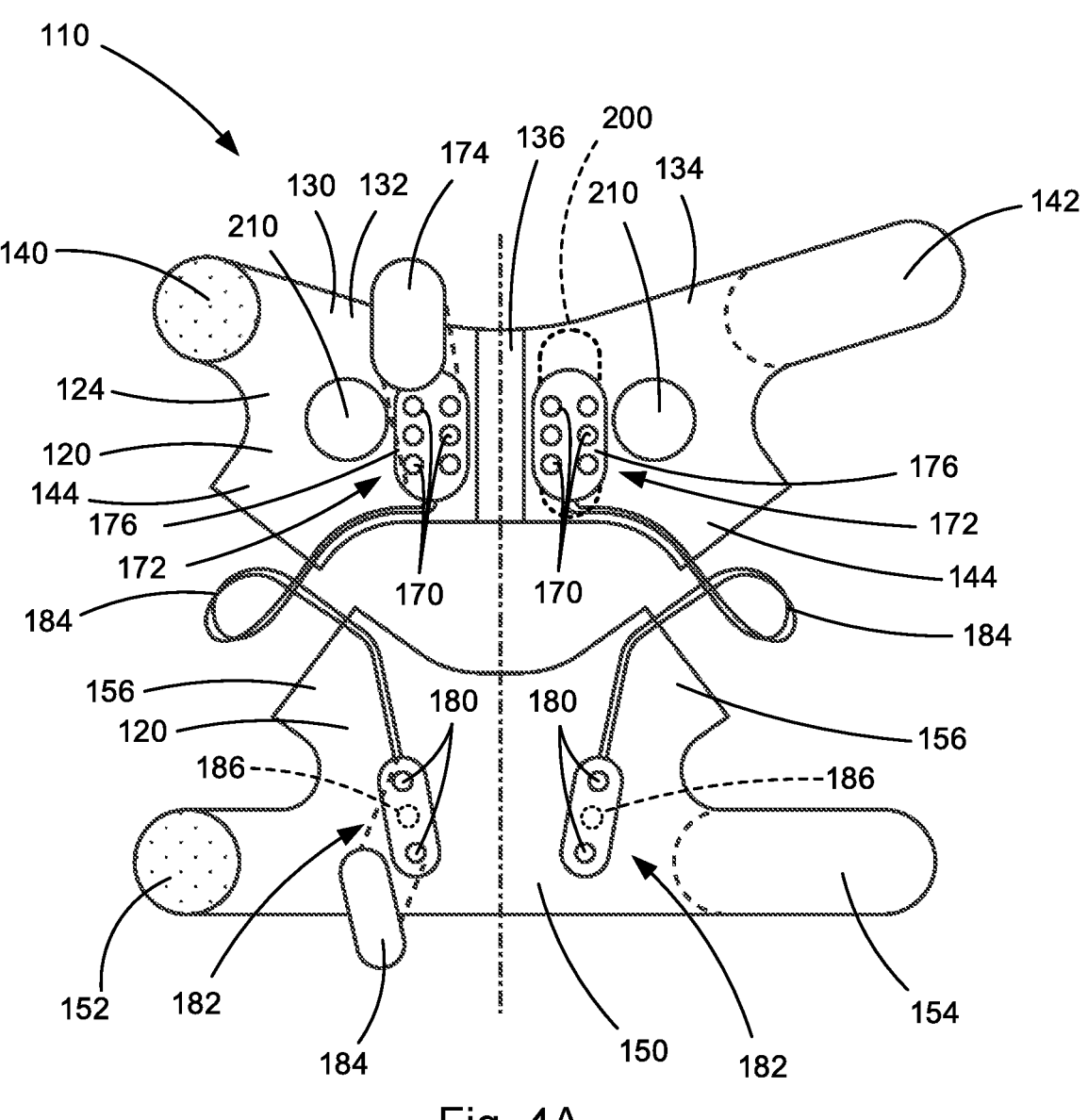

FIG. 4A is an inner surface plan view of components of the electronic medical device of FIGS. 3A and 3B.

Figure 4B:
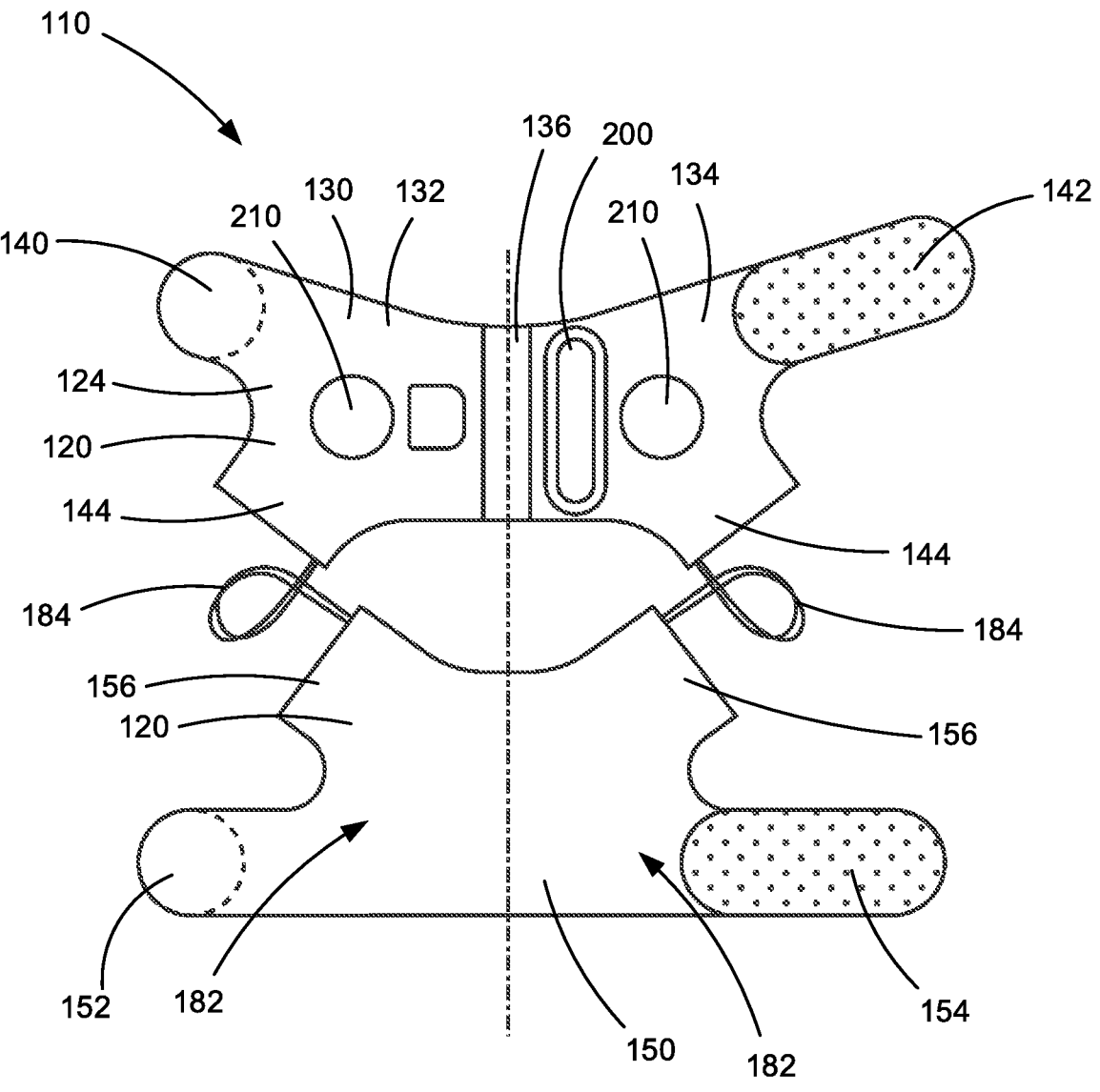

FIG. 4B is an outer surface plan view of the components of the electronic medical device of FIGS. 3A and 3B.

Figure 4C:
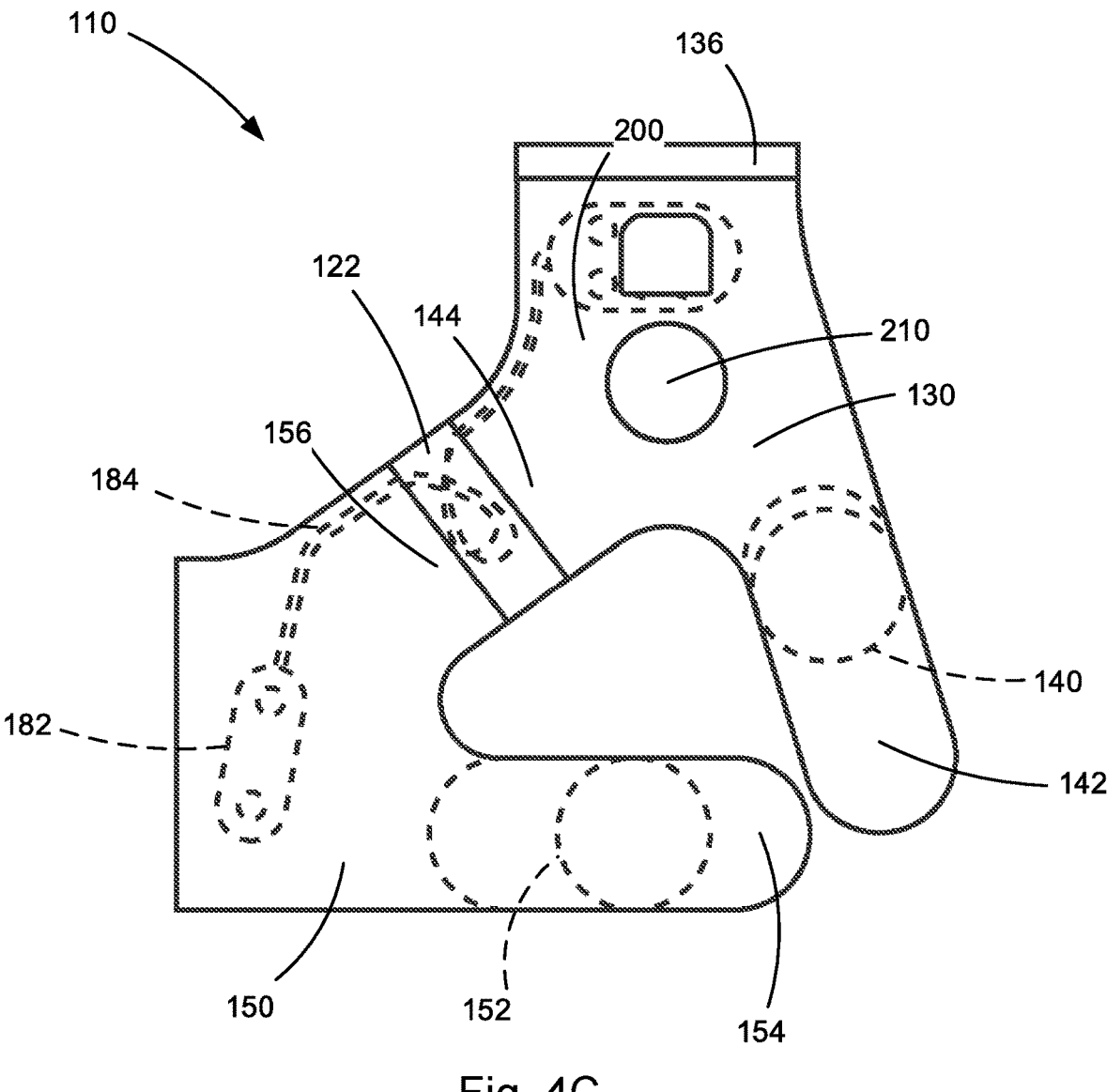

FIG. 4C is an outer surface plan view, taken from a first side, illustrating the components of FIGS. 4A and 4B assembled to form the electronic medical device of FIGS. 3A and 3B.

Figure 4D:
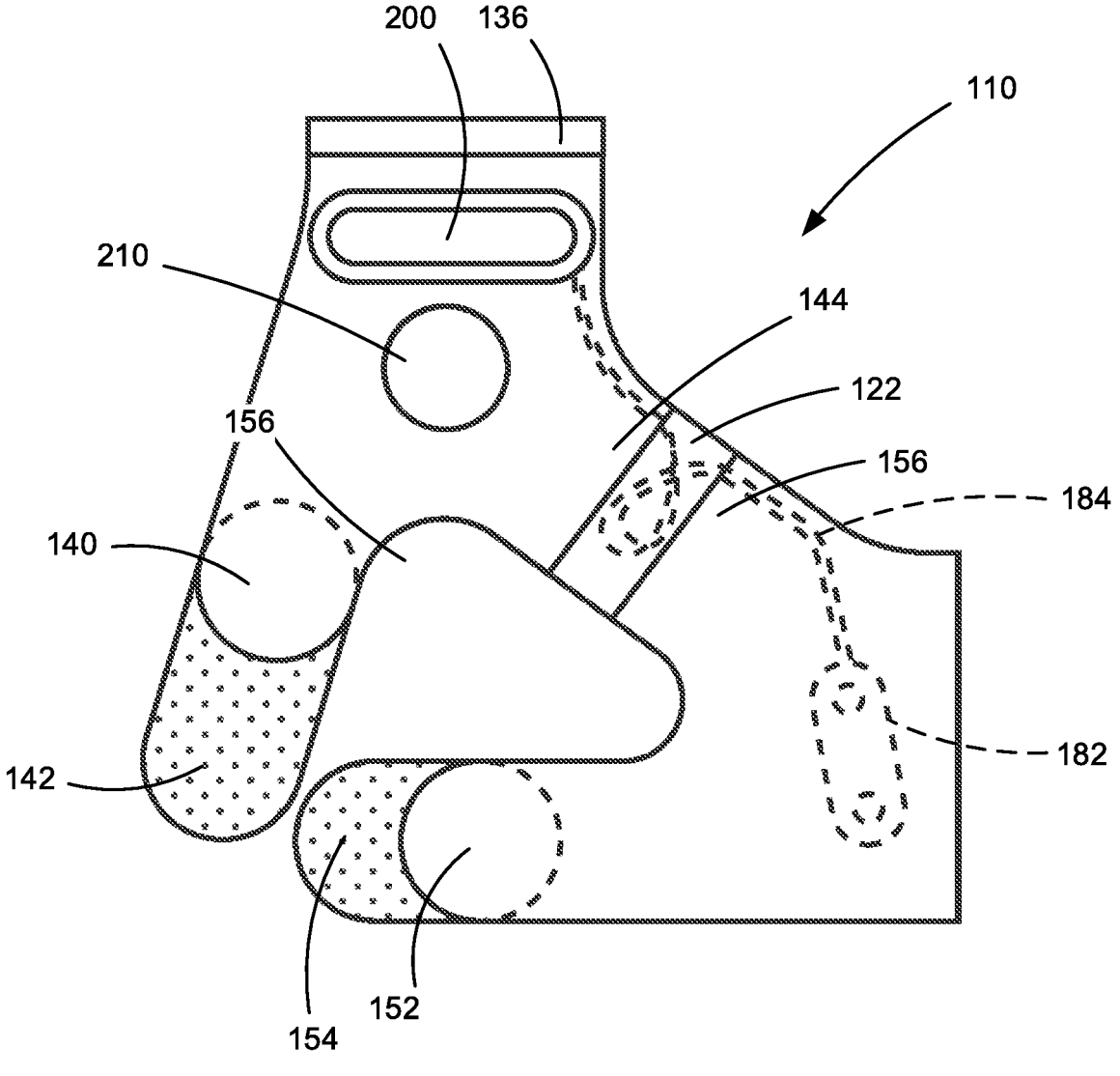

FIG. 4D is an outer surface plan view, taken from a second side, opposite the first side, illustrating the components of FIGS. 4A and 4B assembled to form the electronic medical device of FIGS. 3A and 3B.

Figure 5:
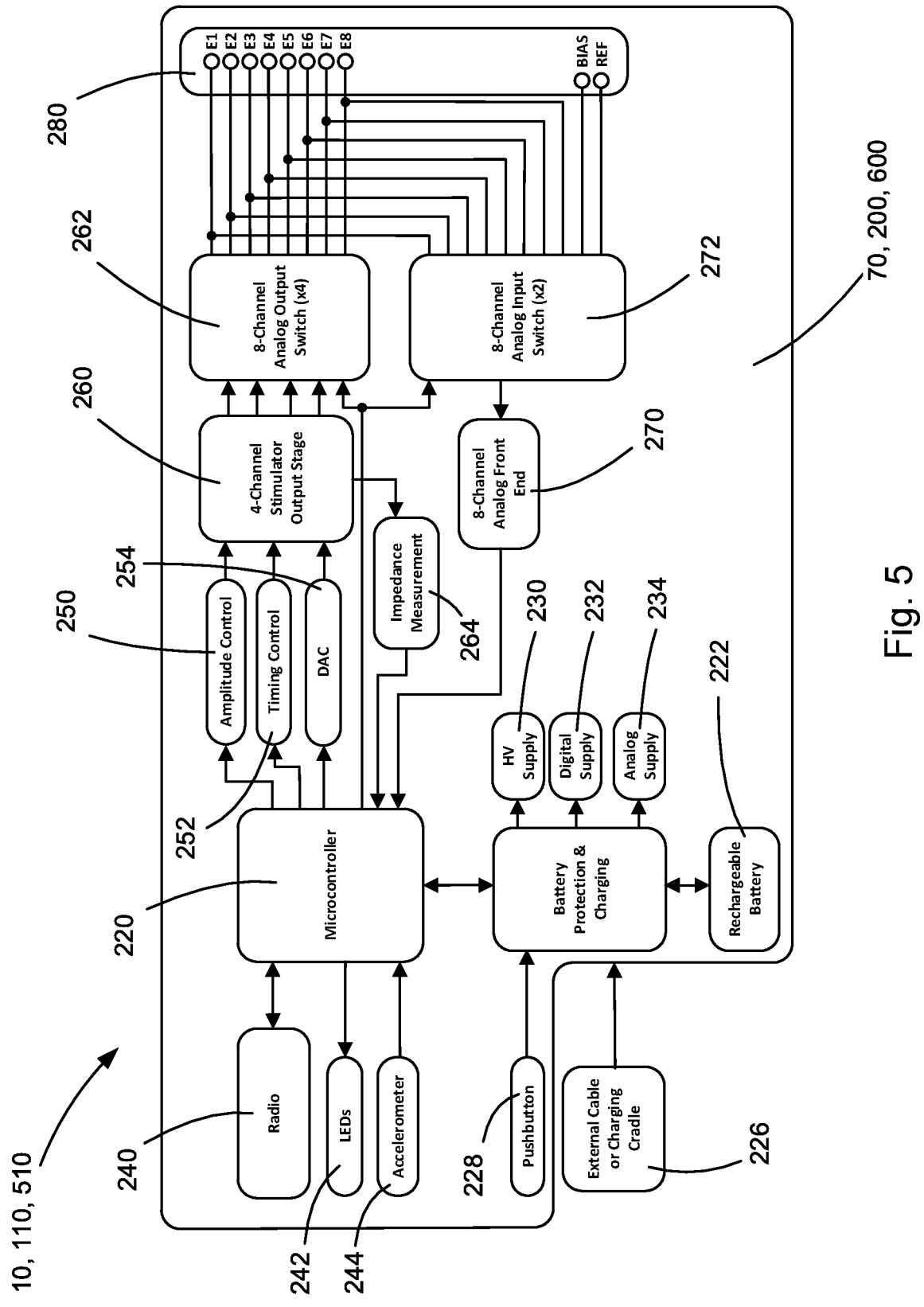

FIG. 5 is a schematic block diagram of a control unit portion of the electronic medical device.

Figure 6:
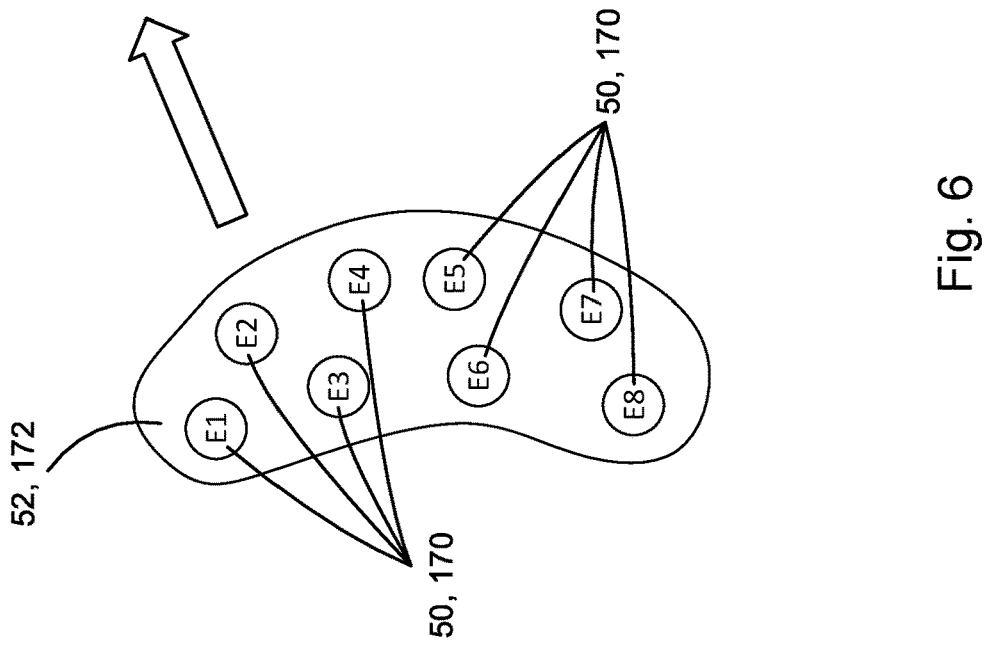

FIG. 6 is a diagram illustrating example electrode arrangements for portions of the electronic medical device.

Figure 7:
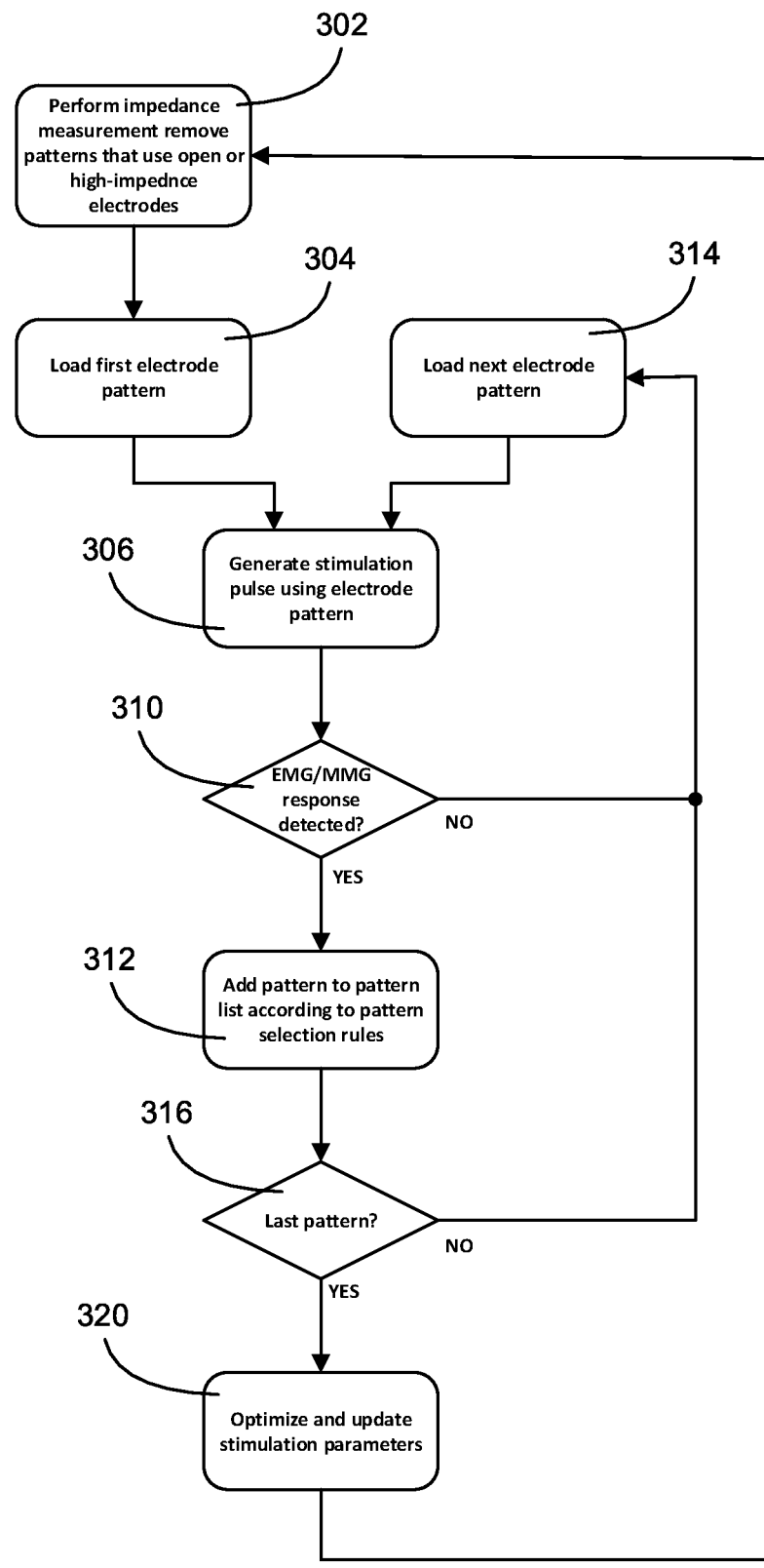

FIG. 7 is a flow chart illustrating an example nerve localization process implemented by the electronic medical device.

Figure 8:
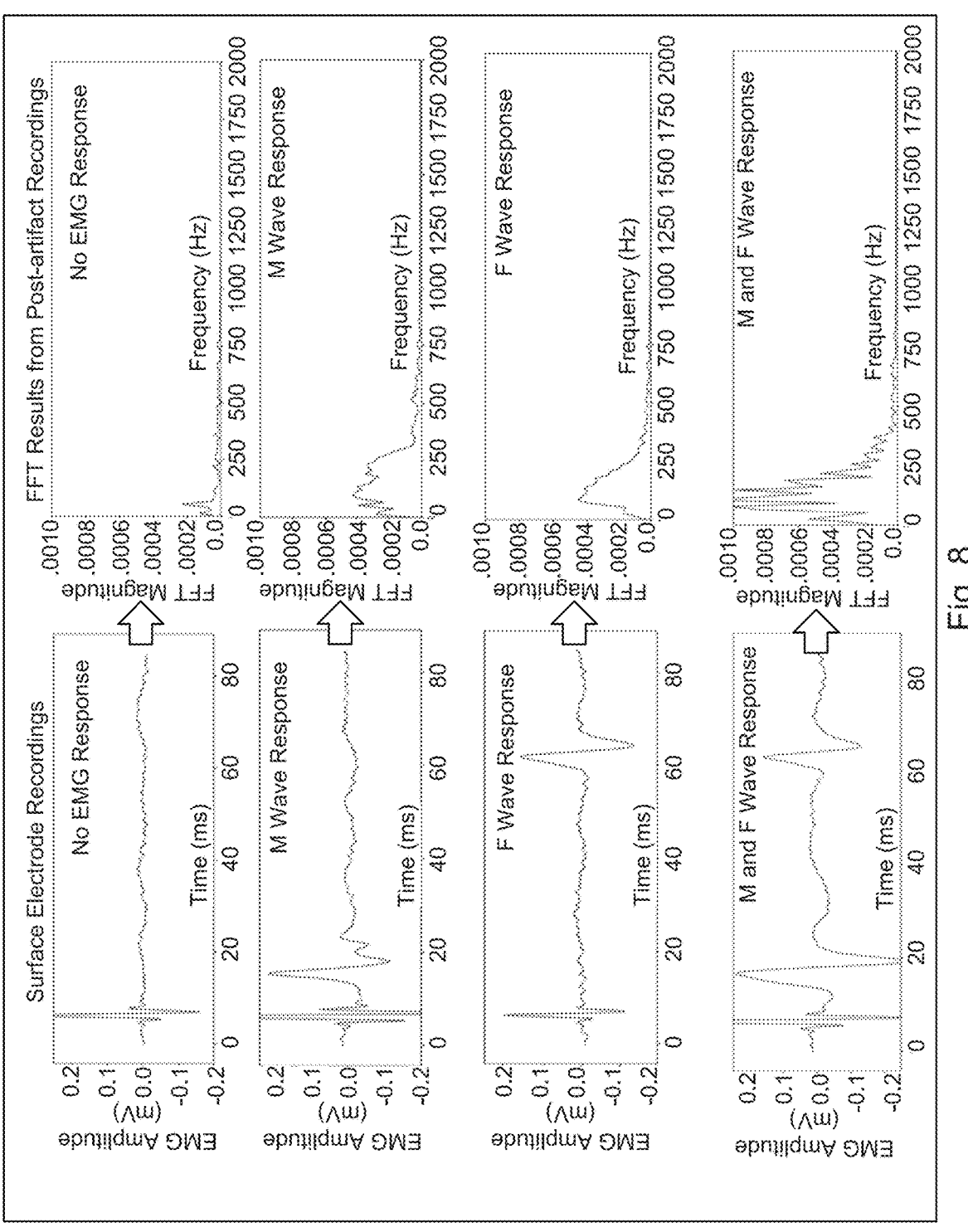

FIG. 8 is a series of charts illustrating examples of recorded EMG responses to electrical nerve stimulation.

Figure 9:
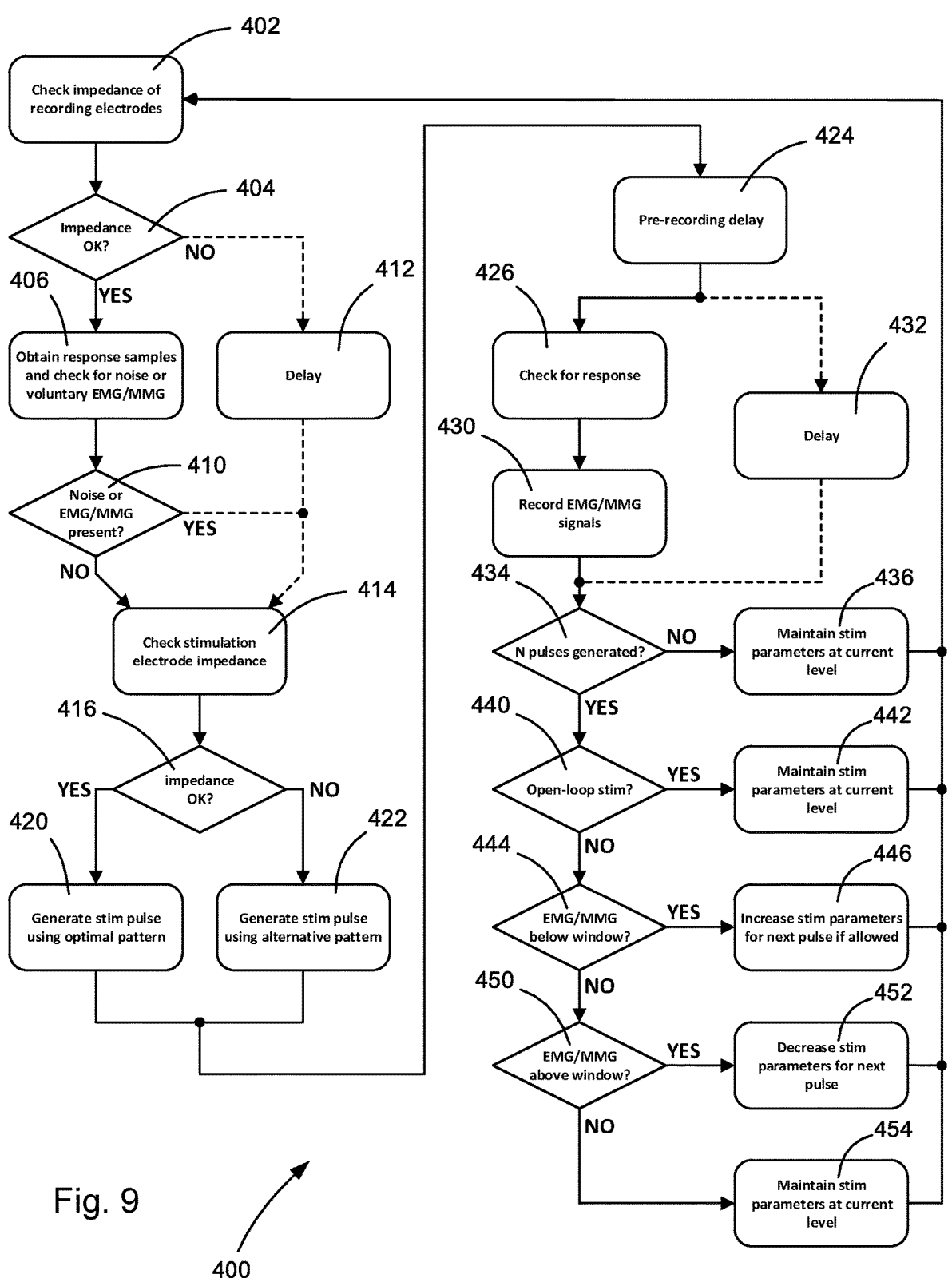

FIG. 9 is a flow chart illustrating an example open-loop and closed-loop electrical nerve stimulation processes implemented by the electronic medical device.

Figures 10A, 10B:
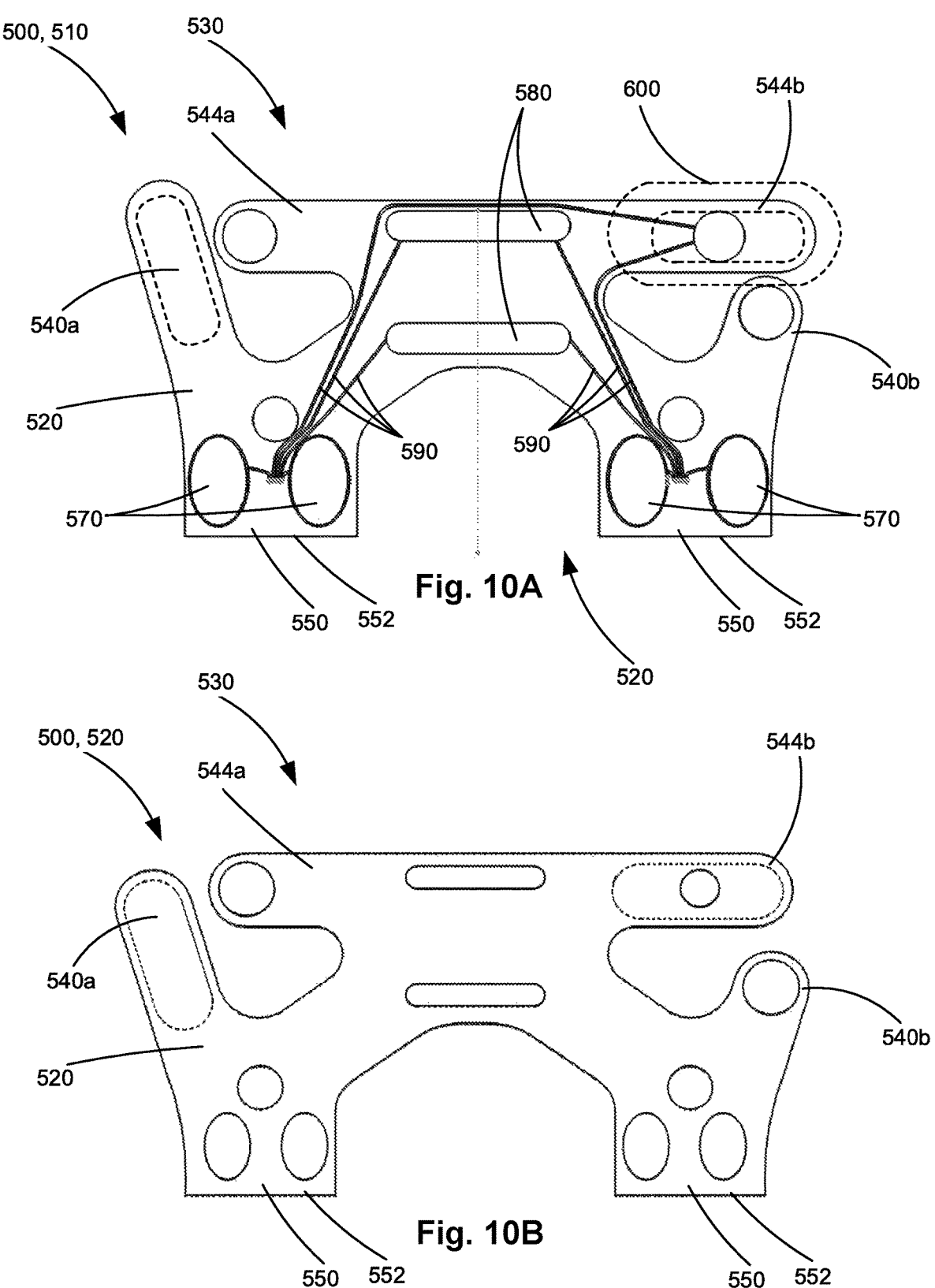

FIG. 10A is a plan view illustrating another example configuration of the electronic medical device.

FIGS. 10B is a plan view illustrating a brace portion of the electronic medical device of FIG. 10A.

Figure 11A:
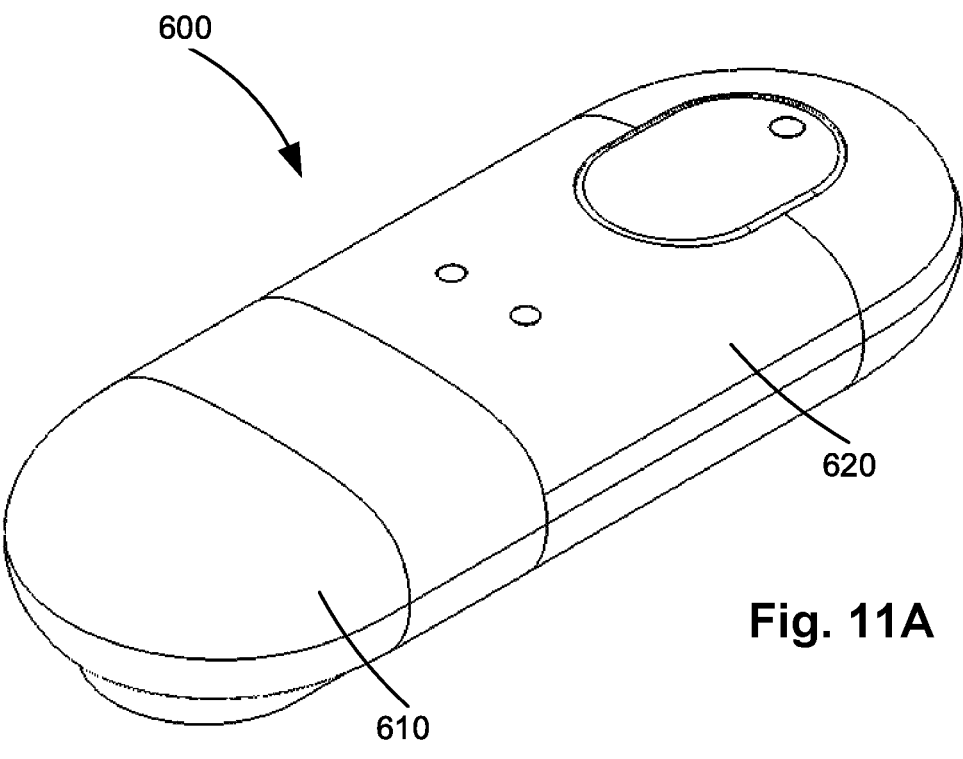
Figure 11B:
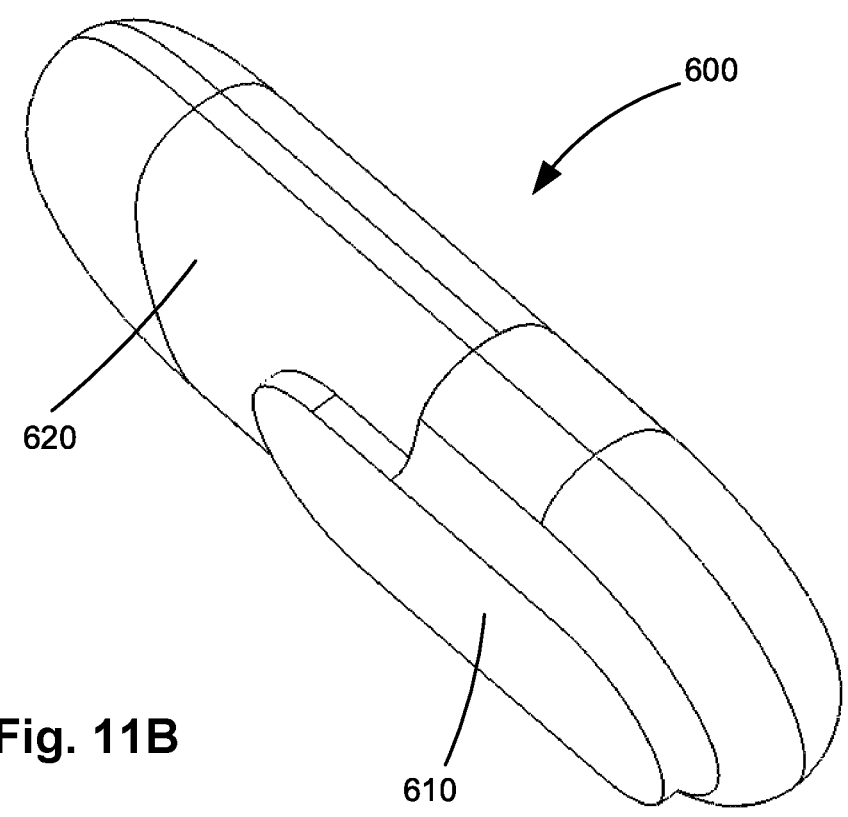
Figures 12A, 12B, 12C, 12D:
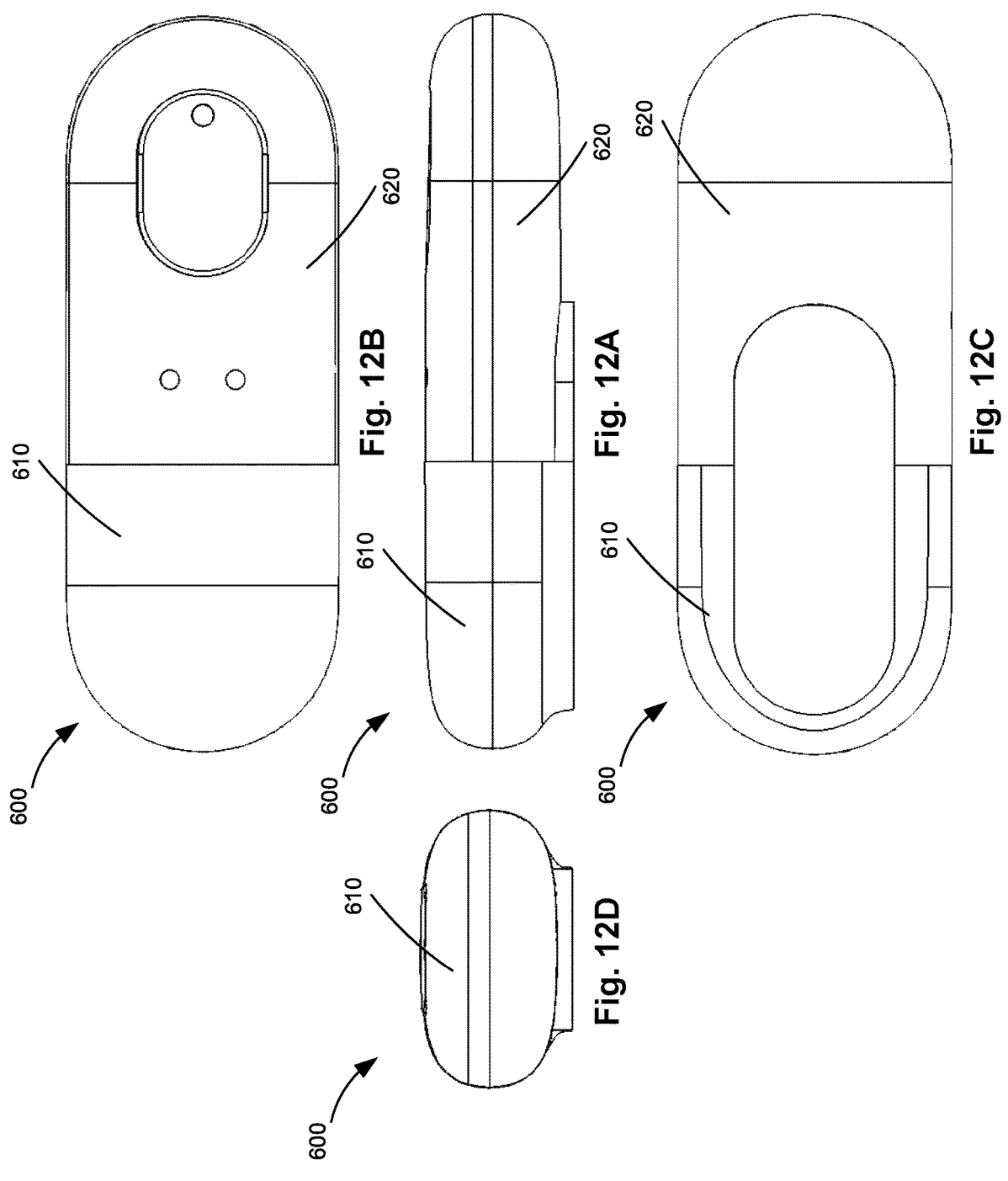

FIGS. 11A-11B are perspective views illustrating a controller portion of the electronic medical device of FIG. 10A.

FIGS. 12A-12D are plan views of the controller illustrated in FIGS. 11A and 11B.

Figure 13A:
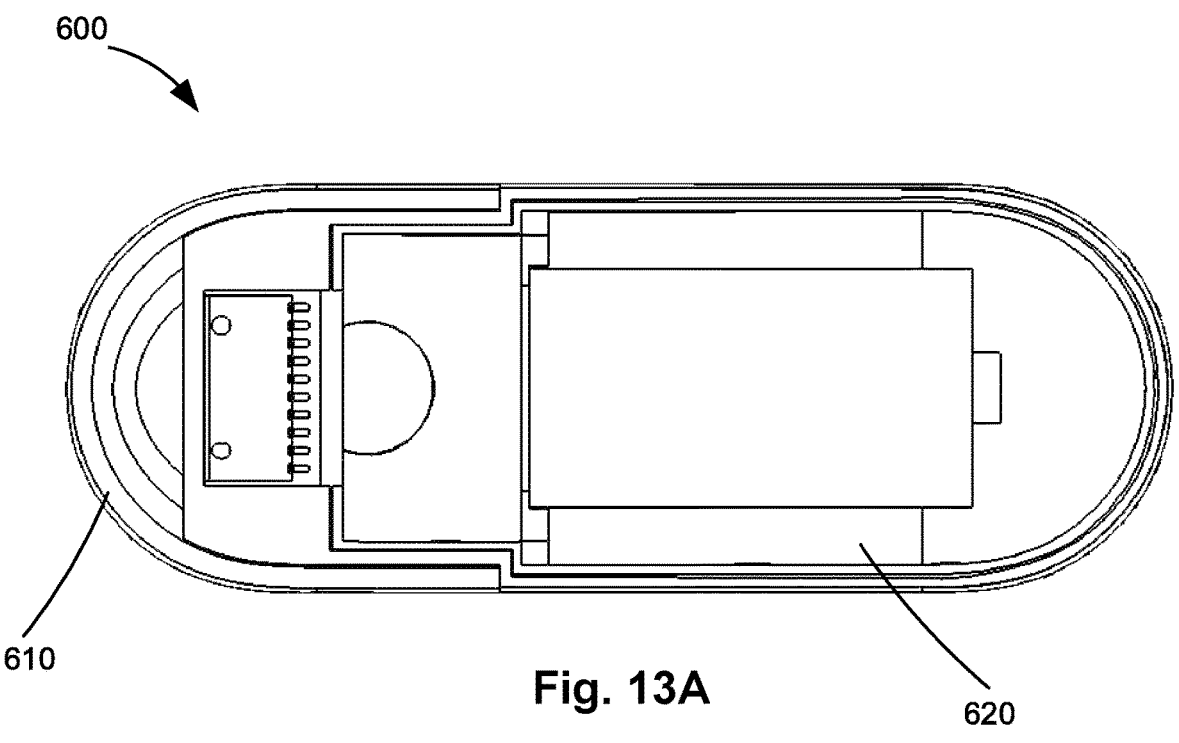
Figure 13B:
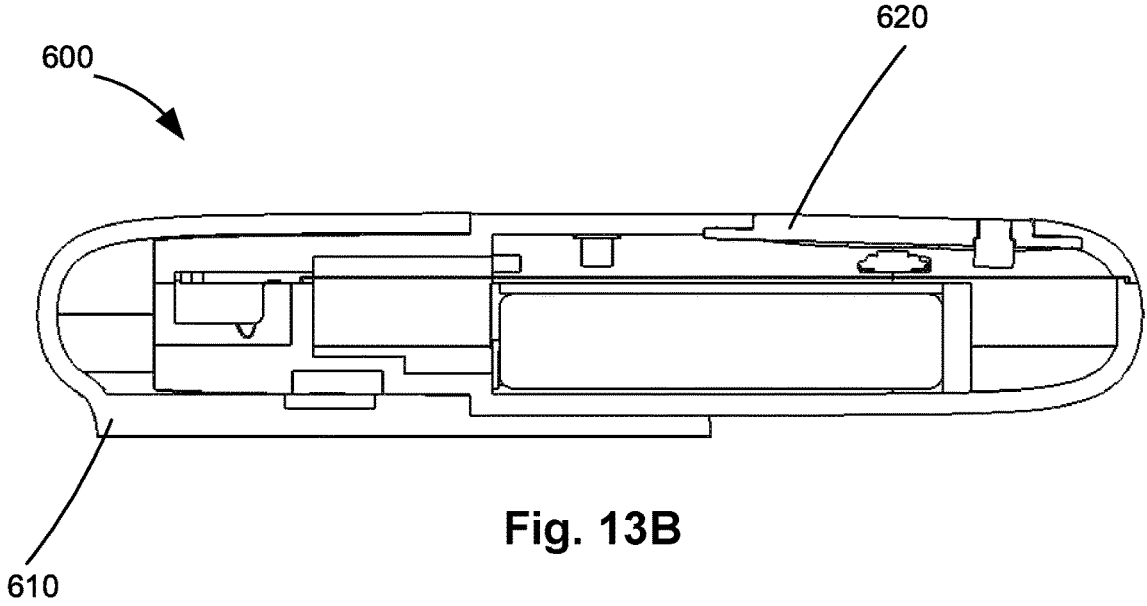

FIGS. 13A-13B are top and side sectional views, respectively, of the controller illustrated in FIGS. 11A and 11B.

Figure 14A:
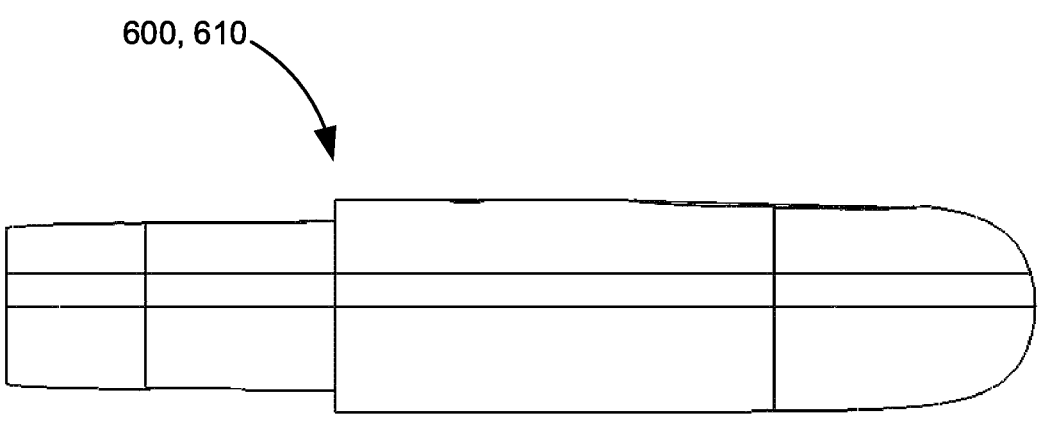
Figure 14B:
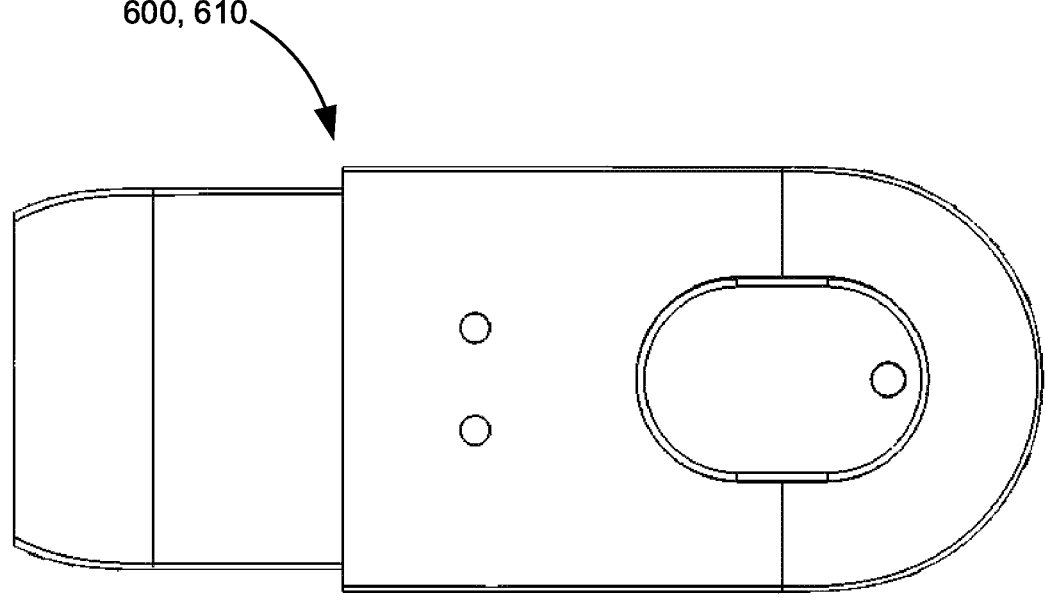
Figure 14C:
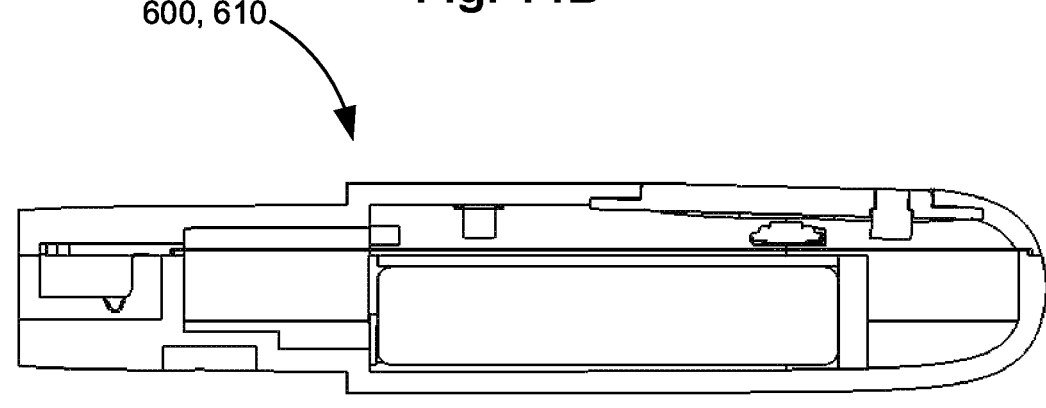

FIGS. 14A-14C are side, top, and side sectional views, respectively, of a portion of the controller illustrated in FIGS. 11A and 11B.

Figure 15:
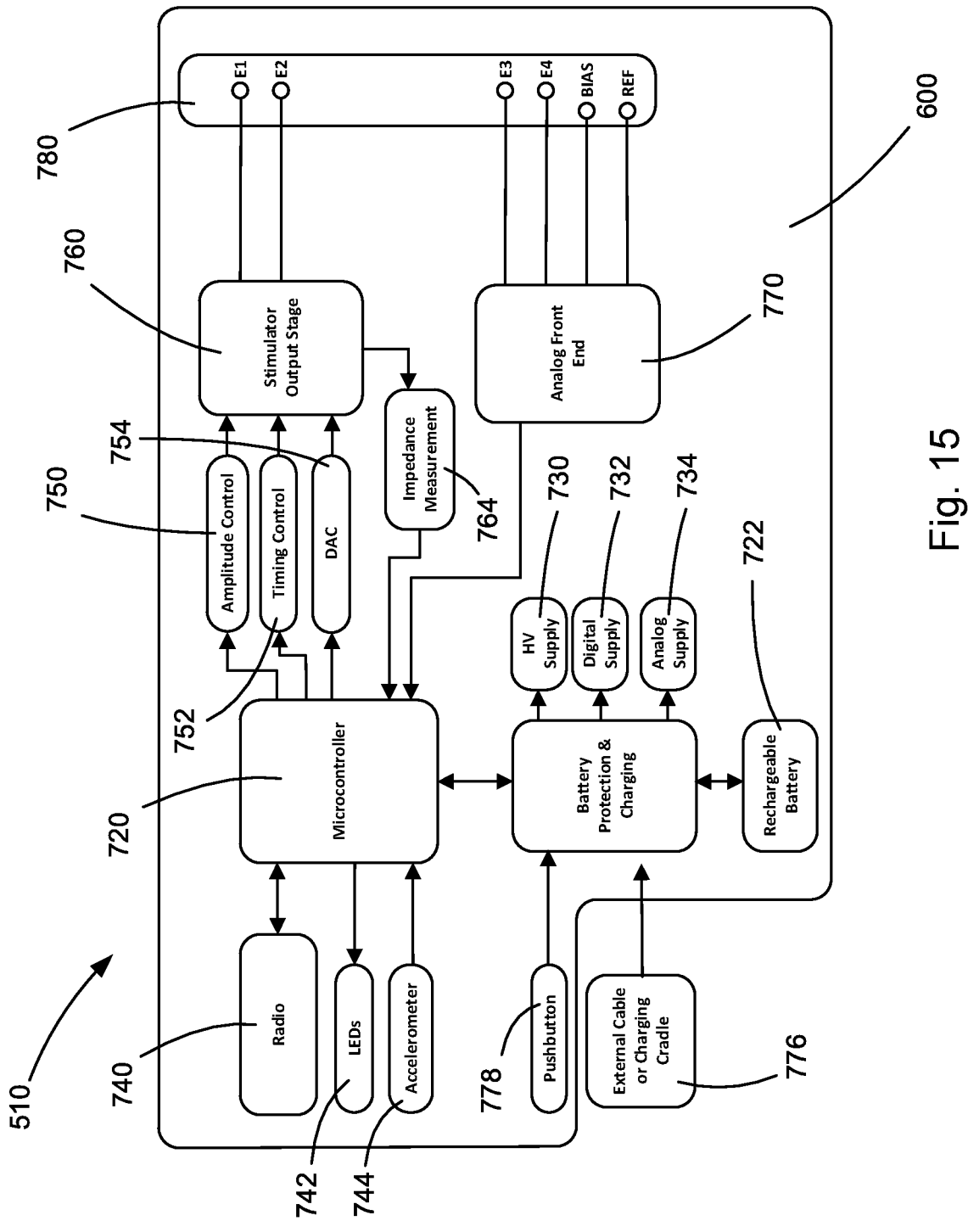

FIG. 15 is a schematic block diagram of a control unit portion of the electronic medical device.

DESCRIPTION

An electronic medical device, a system including the medical device, and a method for using the medical device, is configured to apply electrical stimulation to peripheral nerves to treat various medical conditions. In this description, example configurations of the device, system, and methods are described with reference to the wearable device, illustrated in the accompanying figures, for applying transcutaneous electrical stimulation. All aspects of the invention, however, are not limited to the illustrated wearable transcutaneous stimulation configurations. While these configurations do illustrate some novel physical characteristics of the invention, other novel characteristics, such as stimulation control characteristics, can apply more broadly to other system configurations. For example, the control features/algorithms described herein can be implemented in percutaneous stimulation systems and implanted stimulation systems.

The system can be used to treat a variety of conditions. stimulate the tibial nerve (transcutaneous tibial nerve stimulation "TTNS") to treat medical conditions associated with pelvic floor dysfunction and also to improve pelvic floor function in healthy patients. The electronic medical device applies electrical stimulation near the medial malleolus, which activates both sensory and motor fibers in the nerve. The activation of the sensory fibers of the tibial nerve helps to treat the symptoms of pelvic floor dysfunction.

Pelvic floor dysfunction can include bladder dysfunction and/or bowel dysfunction. Bladder dysfunction includes urinary incontinence such as urge incontinence, overactive bladder (OAB), mixed incontinence, and overflow incontinence. Bladder dysfunction also includes "voiding dysfunction," which refers to urinary incontinence, urinary retention conditions, high urinary frequency, high or low frequency of voiding, an underactive bladder, symptoms of bladder/pelvic pressure/pain, detrusor hyperreflexia, and voiding disorders caused by nerve damage, including interstitial cystitis. With respect to an underactive bladder, the system can be used to apply electrical stimulation to the tibial nerve, for example, to encourage the release of urine for patients with an underactive bladder.

Regarding improving pelvic floor function in a healthy patient (i.e. those without an underlying pelvic floor disorder), the system can be used to apply electrical stimulation to the tibial nerve, for example, in order to temporarily decrease the urge to urinate. In such an aspect, a healthy patient can apply electrical stimulation voluntarily when the patient wants additional bladder control.

Bowel dysfunction includes constipation (including idiopathic constipation), fecal incontinence, and problems with fecal movement, voiding and containment. Without wishing to be bound by theory, it is believed that tibial nerve stimulation can help to strengthen the pelvic floor muscles and sphincter complex to improve fecal incontinence. As such, improving pelvic floor dysfunction can also include modulating contraction of the pelvic floor or "pelvic diaphragm." Over time, therapy may cause contractions that restore the strength of pelvic organs and muscles, which may be a goal of the therapy. Stimulation induced modulation of the pelvic floor, sphincter or other targets can alleviate or eliminate many symptoms of urinary/fecal disorders.

The system also can be used to apply electrical stimulation to the tibial nerve, for example, to improve sexual dysfunction. Tibial nerve stimulation also can be used to improve genital arousal aspects of female sexual interest/ arousal disorder by improving, for example, pelvic blood flow.

The system further can be used to apply electrical stimulation to the tibial nerve, for example, to improve plantar fasciitis. The system also can be applied to the wrist area to provide stimulation to the ulnar nerve and/or median nerve, for example. The stimulation electrodes can, for example, be placed on the inside of the lower arm anywhere 0 to 20 cm from the wrist line. EMG recording electrodes can be placed on the base of thumb to record signal from the abductor/ flexor pollicis brevis. EMG recording electrodes alternatively or additionally can be placed on the base of the fifth digit to record signal from the abductor/flexor digiti minimi brevis. The nerve activation can be confirmed by recording M-wave and F-wave EMG signals from the relevant muscles. The EMG signal can also be used as a control signal to adjust the stimulation parameters. This technology can be applied to median nerve activation, for example, for pain management in carpal tunnel syndrome, hypertension management, and nerve conduction study/nerve injury diagnosis for median/ulnar nerve neuropathy, etc.

The system also can be used to apply transcutaneous electrical stimulation to provide neurostimulation to peripheral nerves in order to enhance nerve regeneration after peripheral nerve injury. Furthermore, the system can be used to apply electrical stimulation to peripheral nerves to improve peripheral nerve pain. Additionally, the system can be used to treat pelvic pain. Furthermore, the system can be used to treat peripheral neuropathy.

The system and/or the device employed by the system can have a variety of implementations. According to one implementation, the electronic medical device (i.e., the electrodes, control unit, wiring, etc.) can be fixed to a garment that is worn by the subject. The garment can be tight or snug-fitting so as to maintain sufficient contact between the subject's skin and can be configured to position the electrodes at locations specific to the peripheral nerves being stimulated. For example, to stimulate peripheral nerves in the area of the foot or ankle, such as the tibial nerve near the medial malleolus as described above, the garment can be in the form of a sock, ankle brace, strap, sleeve, or other like structure. For stimulating peripheral nerves on the leg, the garment can be a brace, strap, or sleeve sized appropriately for lower leg, knee, or upper leg positioning. For knee or ankle positioning, the garment can be configured, e.g., with openings, slots, or interconnected sections, to allow for bending with the joint while maintaining electrode positioning and contact.

Similarly, for stimulating peripheral nerves on the hand, the garment can be in the form of a glove, mitten, hand brace, or sleeve. For stimulating peripheral nerves on the arm, the garment can be a tight/snug fitting brace, strap, or sleeve (e.g., neoprene) that is sized appropriately for lower arm (forearm/wrist), elbow, or upper arm positioning. For wrist and/or elbow positioning, the sleeve can be configured, e.g., via openings, slots, or interconnected sections, to allow for bending with the joint while maintaining electrode positioning and contact.

In keeping with the above, it will be appreciated that the manner in which the electronic medical device can be secured or supported on the subject can vary. It will also be appreciated that the manner in which the electronic medical device is supported is not critical, as long as contact between the electrodes and the subject's skin is maintained, the positions of the electrode on the subject are maintained, and that the aforementioned are achieved in a manner that is comfortable to the subject.

Strap Implementation

FIGS. 1A-B illustrate a system comprising an example configuration of the electronic medical device 10 for providing transcutaneous electrical nerve stimulation, referred to herein as a neurostimulator, supported on a subject 12. The neurostimulator 10 of FIGS. 1A-B includes a garment in the form of a strap 20 that supports the neurostimulator and its components on the subject 12. In the example configuration of FIGS. 1A-B, the strap 20 connects the neurostimulator 10 to the subjects foot 14, with FIG. 1A illustrating a left foot implementation, and FIG. 1B illustrating a right foot implementation. In both instances, the strap 20 is wrapped figure-eight style, with one loop extending around the foot and one loop extending around the lower leg/ankle. Opposite end portions of the strap 20 can be interconnected, e.g., via a buckle or loop 22 and an end portion 24 of the strap that extends through the loop, is folded over, and connected to itself with a hook and loop fastener. The hook and loop fastener is shown in FIG. 2B and includes a hook portion 26 and loop portion 28.

The strap 20 implementation of the neurostimulator 10 is advantageous in that it is versatile and can be adapted to secure the neurostimulator to a wide variety of locations on the subject 12. The strap 20 can easily be wrapped around the foot 14 and/or ankle 16, as shown, and can also be wrapped around and secured to any location along the length of the subject's leg 18, either in a single loop or more than one loop, as the length of the strap permits. At the knee, the strap 20 can be wrapped, for example, in a figure-eight style in a manner similar to that illustrated in FIGS. 1A and 1B.

Referring to FIGS. 2A-B, the neurostimulator 10 includes a several of components that are secured or otherwise supported on the strap 20. The securement of these components can be achieved in a variety of manners, such as by adhesives, stitching, mechanical fastening, hook and loop fasteners, or a combination thereof.

The neurostimulator 10 includes stimulation electrodes 50. In this example implementation, the stimulation electrodes 50 are arranged in one or more arrays 52 and positioned on an inner surface 36 of the strap 20 at a widened end portion 30 of the strap. The number of stimulation electrodes 50 (i.e., 2 or more), the area covered by the electrodes 50 and/or the electrode array 52, the electrode density (i.e., number of electrodes per unit area)of an electrode array, and the distribution or pattern of electrodes within an electrode array all can vary depending on the intended application of the neurostimulator 10. Additionally, the neurostimulator 10 can include more than one stimulation electrode array 52 again, depending on the application. In the example configuration of FIG. 2A, the stimulation electrode array 52 includes six stimulation electrodes 50 arranged in a generally elongated kidney-shaped manner. The number and arrangement of the stimulation electrodes 50, and the location/position of the electrodes 50 and electrode array 52 on the strap 20 are by way of example only and are by no means limiting.

In the example configuration of FIG. 2A, the stimulation electrodes 50 can be dry electrodes, in which case the neurostimulator 10 can include a removable/replaceable stimulation gel pad 54 shaped and sized to coincide with and cover the stimulation electrodes 50. In use, the gel pad 54 facilitates a strong, reliable electrical connection between the stimulation electrodes 50 and the subject's skin.

The neurostimulator 10 also includes dedicated recording electrodes 60. In this example implementation, the recording electrodes 60 are arranged in one or more arrays 62 and positioned on the inner surface 36 of the strap 20 spaced from the stimulation electrode array 52. The spacing between the stimulation electrodes 50 and the recording electrodes 60 can be important, as it can be necessary to provide adequate distance between the electrodes so that electrical stimulation signals can be separated or distinguished from responses (e.g., neurological, muscular, neuromuscular, etc.) to those electrical stimulation signals. This facilitates utilizing responses to stimulation sensed by the recording electrodes 60 as feedback in a closed-loop stimulation control scheme, which is described in detail below.

The number of recording electrodes 60 (i.e., one or more), the area covered by the electrodes 60 and/or the electrode array 62, the electrode density (i.e., number of electrodes per unit area) in an electrode array, and the distribution or pattern of electrodes within an electrode array all can vary depending on the intended application of the neurostimulator 10. Additionally, the neurostimulator 10 can include more than one recording electrode array 62 again, depending on the application. In the example configuration of FIG. 2A, the recording electrode array 62 includes four electrodes 60 arranged linearly in two parallel rows of two electrodes. The number and arrangement of the recording electrodes 60, and the location/position of the electrodes 60 and electrode array 62 on the strap 20 are by way of example only and are by no means limiting.

In the example configuration of FIG. 2A, like the stimulation electrodes 50, the recording electrodes 60 can also be dry electrodes. Because of this, the neurostimulator 10 can also include a removable/replaceable gel pad 64 shaped and sized to coincide with and cover the recording electrodes 60. In use, the gel pad 54 facilitates a strong, reliable electrical connection between the recording electrodes 60 and the subject's skin.

Referring to FIG. 2B, the neurostimulator 10 also includes an electronic control unit 70 that is operative to control the application of transcutaneous electrical nerve stimulation via the stimulating electrodes 50 and to receive stimulation feedback gathered by the recording electrodes 60. The control unit 70 is located at the widened end 30 of the strap 20 on an outer surface 38, opposite the inner surface 36, of the strap 20. The buckle 22 can be a portion of the control unit 70 or can be connected to the control unit. In the example configuration of FIG. 2B, the control unit 70 has a generally elongated kidney-shaped configuration similar to that of the stimulating electrode array 52 and is positioned on the outer surface 38 generally opposite the stimulating electrode array. This is by no means necessary to the design of the neurostimulator 10, as the shape and location of the control unit 70 can vary.

In the example configuration of FIG. 2B, however, the shape and the positioning of the control unit 70 is convenient. The control unit 70 is detachably connected to the remainder of the neurostimulator 10 via a plug-in or snap-in connector 72 (see FIG. 2B), which receives a mating connector 74 (see FIG. 2D) on the control unit 70. FIG. 2B shows the control unit 70 connected to the neurostimulator 20 via the connector 72, and FIG. 2C shows the neurostimulator 20 with the control unit detached from the connector and removed. Configuring the control unit 70 to be detachable/removable allows the control unit to be utilized with other neurostimulator configurations and also allows the strap 20 and the components remaining on the strap (e.g., the electrodes, etc.) to be replaced when worn out, expired, or otherwise due for replacement.

Advantageously, the stimulating electrodes 50 can be part of an assembly in which the stimulating electrodes 50 can be mounted on a substrate or housing 56 constructed, for example of plastic. This substrate/housing 56 can itself be secured to the strap 20 (e.g., via adhesives, stitching, or mechanical fastening) to thereby secure the stimulation electrodes 50 to the strap. Forming the stimulating electrodes 50 in this manner facilitates a precise arrangement and spacing of the stimulation electrodes 50 and makes it easy to secure them to the strap 20.

The connector 72 can also be formed as a portion of the housing 56. The connector 72 can be configured to protrude from a side of the housing 56 opposite the stimulation electrodes 50. The connector 72 can, for example, extend through a hole in the strap 20 to position the connector on or extending from the outer surface 38. When the control unit 70 is connected to the connector 72, the strap 20 can be positioned between the control unit and the portion of the housing 56 supporting the stimulator electrodes 50.

The connector 72 can support a plurality of terminals for electrically connecting the control unit 70 to the stimulation electrodes 50 and the recording electrodes 60. Certain terminals in the connector 72 can be electrically connected to the stimulation electrodes 50 by wires or leads that are embedded within the plastic housing material (e.g., via insert molding). Embedding the leads in this manner helps maintain adequate spacing between the conductors, which avoids the potential for shorts in the circuitry.

Other terminals in the connector can be electrically connected to the recording electrodes 60 by wires or leads 66 that are partially embedded within the plastic housing material (e.g., via insert molding) and pass through the housing 56, extending to the feedback electrodes 60. Through this configuration, all of the necessary electrical connections to the stimulation and recording electrodes 50, 60 are made when the control unit 70 is installed on the connector 72.

The neurostimulator 10 also includes electrode backing 80 that facilitates safe storage and portability of the system. Fold lines 82, 84 shown in FIG. 2A indicate lines along which the neurostimulator 10/strap 20 can be folded to place the device in the stored condition. The steps involved in placing the neurostimulator 10 in the stored condition are illustrated in FIGS. 2C-2E.

As shown in FIG. 2C, the control unit 70 is detached from the housing 56. The control unit 70 is secured to the end portion 24 of the strap 20 by the hook and loop fastener 26, 28. Next, as shown in FIG. 2D, with the inner surface 36 facing up, the widened end portion 38 is folded over along the fold line 82, which places the stimulating electrodes 50 on a corresponding portion of the electrode backing 80. Next, as shown in FIG. 2E, the strap 20 is folded over along the fold line 84, which places the recording electrodes 60 on a corresponding portion of the electrode backing 80. This leaves the neurostimulator 10 in the stored condition of FIG. 2E.

To use the neurostimulator 10, the strap 20 is simply unfolded and the control unit 70 is connected to the housing 56 via their respective connectors 72, 74. The hook and loop fastener 26, 28 can be disconnected, the strap 20 wrapped around the appropriate anatomy of the subject, and the fastener re-connected to attach neurostimulator 10 to the subject. Conveniently, where the neurostimulator 10 is configured for stimulating the tibial nerve in the position illustrated in FIGS. 1A-B, the widened end 30 of the strap 20 can include a visual alignment cue 90, such as a hole in the strap, that becomes aligned with the medial malleolus of the ankle when the stimulating electrodes are properly positioned.

Brace Implementation

FIGS. 3A-B illustrate a system comprising another example configuration of an electronic medical device 110 for providing transcutaneous electrical nerve stimulation, referred to herein as a neurostimulator, supported on a subject 112. The neurostimulator 110 of FIGS. 3A-1B includes a garment in the form of a brace 120 that supports the neurostimulator and its components on the subject 112. In the example configuration of FIGS. 3A-B, the brace 120 connects the neurostimulator 110 to the subject's foot 114, with FIG. 3A illustrating a left foot implementation, and FIG. 3B illustrating a right foot implementation. In both instances, the brace 120 has an upper portion 130 wrapped around the lower leg/ankle and a lower portion 150 portion wrapped around the foot/ankle. Each of these portions are secured to the subject via a connection such as a hook and loop fastener.

The brace 120 implementation of the neurostimulator 10 is advantageous in that it is versatile in its ability to position the stimulating electrodes and recording electrodes at different locations on the subject. For example, stimulating electrodes can be positioned on the upper portion 130 of the brace 120 wrapped around the ankle, and recording electrodes can be positioned on the lower portion 150 of the brace wrapped around the foot. This can be especially advantageous for closed-loop neurostimulation of the tibial nerve. In this implementation, stimulating electrodes on the upper portion 130 can be located between the medial malleolus and the Achilles tendon to provide electrical stimulation to the tibial nerve. Recording electrodes on the lower portion 150 can be located on the bottom of the subject's foot, near the flexor muscles (abductor hallucis and the flexor hallucis brevis) for the big toe and can record the EMG signals that result from recruitment of the tibial nerve's motor fibers.

As another advantage, the brace 120 is configured for placement at or about a subject's joint and provides for movement of that joint. While the brace 120 is illustrated as being applied at the subject's ankle joint, it will be appreciated that the brace 120 can also be applied at the knee joint or elbow joint. Additionally, positioning the brace 120 at a joint is not critical, as it can be seen that the brace can be applied at any location along the subject's arms or legs, size permitting.

The construction of the neurostimulator 110 is illustrated in FIGS. 4A-D. For the example configuration of FIGS. 4A-D the upper portion 130 and lower portion 150 of the strap 120 are separate components that are interconnected by adjustment bands 122. The adjustment bands 122 can allow for adjusting the spacing between the upper and lower portions 130, 150, e.g., via a buckle or hook and loop fastener, or the bands can be of a fixed size amongst a range of sizes, e.g., x-small, small, medium, large, x-large, etc. The respective sizes of the upper and lower portions 130, 150 can be similarly sized. In fact, the upper portion 130 can itself be composed of first and second portions 132, 134 connected by a band 136 that allows for adjusting the spacing between the upper and lower portions 130, 150, e.g., via a buckle or hook and loop fastener.

The upper portion 130 of the brace 120 includes a hook and loop fastener composed of a hook portion 140 and a loop portion 142, which are positioned opposite each other along an upper extent of the upper portion. The upper portion 130 also includes opposite tab portions 144 to which the adjustment tabs 122 (see, FIGS. 4C-D) are connected, e.g., via stitching. Similarly, the lower portion 130 of the brace includes a hook and loop fastener composed of a hook portion 152 and a loop portion 154, which are positioned opposite each other along a lower extent of the lower portion. The lower portion 150 also includes opposite tab portions 156 to which the adjustment tabs 122 (see, FIGS. 4C-D) are connected, e.g., via stitching.

The neurostimulator 110 includes a several of components that are secured or otherwise supported on the brace 120. The securement of these components can be achieved in a variety of manners, such as by adhesives, stitching, mechanical fastening, hook and loop fasteners, or a combination thereof. FIGS. 4A and 4B illustrate the neurostimulator 110 in a partially assembled condition, with the electronic components of the neurostimulator mounted on the brace 120 prior to the first and second portions 132, 134 being interconnected by the adjustment bands 122. This construction is advantageous because it allows the electronic components of the neurostimulator 110 to be assembled onto brace 120 while the upper and lower portions 130, 150 lie flat. The lying flat illustration of FIGS. 4A-B is for purposes of simplicity as it allows the upper and lower portions 130, 150 to be illustrated lying flat. FIG. 4A illustrates an inner surface 124 of the brace 120. FIG. 4B illustrates an outer surface 126 of the brace 120.

The neurostimulator 110 includes stimulation electrodes 170. In this example implementation, the stimulation electrodes 170 are arranged in one or more arrays 172 and positioned on the inner surface 124 of the upper portion 130 of the brace 120. In the example configuration illustrated in FIG. 4A, the stimulation electrodes 170 are positioned on opposite sides of the adjustment band 136 connecting the first and second portions 132, 134 of the upper portion 130. This arrangement can, for example, allow the brace 130 implementation of the neurostimulator 110 to be ambidextrous.

The number of stimulation electrodes 170 (i.e., 2 or more), the area covered by the stimulation electrodes 170 and/or the electrode arrays 172, the electrode density (i.e., number of electrodes per unit area) of the arrays, and the distribution or pattern of electrodes within an array all can vary depending on the intended application of the neurostimulator 110. In the example configuration of FIG. 4A, each stimulation electrode array 172 includes six stimulation electrodes 170 arranged in a generally rectangular manner in two rows of three electrodes. The number and arrangement of the stimulation electrodes 170, and the location/position of the electrode array 172 on the brace 120 are by way of example only and are by no means limiting.

In the example configuration of FIG. 4A, the stimulation electrodes 170 can be dry electrodes, in which case the neurostimulator 110 can include one or more removable/replaceable stimulation gel pads 174 shaped and sized to coincide with and cover the stimulation electrode array 172. In use, the gel pads 174 facilitate a strong, reliable electrical connection between the stimulation electrodes 170 and the subject's skin.

The neurostimulator 110 also includes recording electrodes 180. In this example implementation, the recording electrodes 180 are arranged in one or more arrays 182 and positioned on the inner surface 124 of the lower portion 150 of the brace 120 at a location spaced from the stimulation electrodes 170. The spacing between the stimulation electrodes 170 and the recording electrodes 180 can be important, as it can be necessary to provide adequate distance between the electrodes so that electrical stimulation signals can be separated or distinguished from responses (e.g., neurological, muscular, neuromuscular, etc.) to those electrical stimulation signals. This facilitates utilizing responses to stimulation sensed by the recording electrodes 180 as feedback in a closed-loop stimulation control scheme which, again, is described in detail below.

The number of recording electrodes 180 (i.e., 1 or more), the area covered by the recording electrodes 180 and/or the electrode array 182, the electrode density (i.e., number of electrodes per unit area) in an array, and the distribution or pattern of electrodes within an array all can vary depending on the intended application of the neurostimulator 110. In the example configuration of FIG. 4A, there are two recording electrode arrays 182, each of which includes two recording electrodes 180 arranged linearly. The number and arrangement of the recording electrodes 180, and the location/position of the electrode arrays 182 on the brace 120 are by way of example only and are by no means limiting.

In another implementation, the neurostimulator 110 can be configured to include MMG sensors (e.g., accelerometers) for sensing muscle movement as opposed to electrical activity. The optional MMG sensors are illustrated in dashed lines at 186 in FIG. 4A. In this implementation, the MMG sensors 186 can be implemented in addition to or in place of, the EMG electrodes 180. Implementing the MMG 186 sensors along with the EMG sensors 180 can prove beneficial in that the combination can provide additional functionality. For example, the MMG sensor 186 can be used to confirm the validity of an EMG measured feedback response. Additionally, the MMG sensors 186 (or any other accelerometer for that matter) can be used to verify that the subject in a resting, i.e., not moving, condition prior to initiating a therapy session.

In the example configuration of FIG. 4A, like the stimulation electrodes 170, the recording electrodes 180 can also be dry electrodes. Because of this, the neurostimulator 110 can also include a removable/replaceable recording gel pad 184 shaped and sized to coincide with and cover the recording electrode arrays 182. In use, the gel pad 184 facilitates a strong, reliable electrical connection between the recording electrodes 180 and the subject's skin.

Referring to FIG. 4B, the neurostimulator 110 also includes an electronic control unit 200 that is operative to control the application of transcutaneous electrical nerve stimulation via the stimulating electrodes 170 and to receive stimulation feedback gathered by the recording electrodes 180. The control unit 200 is located on the outer surface 126 of the upper portion 130 adjacent the adjustment band 136 and opposite one of the stimulating electrode arrays 172 on the inner surface 124 of the upper portion. In the example configuration of FIG. 4B, the control unit 200 has a generally elongated racetrack-shaped configuration similar, to that of the stimulating electrode arrays 172, although narrower. This is by no means necessary to the design of the neurostimulator 110, as the shape and location of the control unit 200 can vary.

In the example configuration of FIG. 4B, however, the shape and the positioning of the control unit 200 is convenient. The control unit 200 can be detachably connected to the remainder of the neurostimulator 110 via a plug-in or snap-in connector, such as by a connector (not shown) that is similar or identical to the connector associated with the control unit of the example configuration of FIGS. 2A-D. Configuring the control unit 200 to be detachable/removable allows the control unit to be utilized with other neurostimulator configurations and also allows the brace 120 and the components remaining on the brace (e.g., the electrodes, etc.) to be replaced when worn out, expired, or otherwise due for replacement.

Advantageously, the stimulating electrodes 170 can be part of an assembly in which the stimulating electrodes 170 can be mounted on a substrate or housing 176 constructed, for example of plastic. This substrate/housing 176 can itself be secured to the brace 120 (e.g., via adhesives, stitching, or mechanical fastening) to thereby secure the stimulation electrodes 170 to be brace. Forming the stimulating electrodes 170 in this manner facilitates a precise arrangement and spacing of the stimulation electrodes 170 and makes it easy to secure them to the brace 120.

In a manner similar or identical to that of the example configuration of FIGS. 2A-D, the connector for the stimulating electrodes 170 can also be formed as a portion of the housing 176. The connector can be configured to protrude from a side of the housing 176 opposite the stimulation electrodes 170. The connector can, for example, extend through a hole in the brace 120 to position the connector on or extending from the outer surface 126. When the control unit 200 is connected to the connector, the brace 120 can be positioned between the control unit and the portion of the housing 176 supporting the stimulator electrodes 170.

Again, in a manner similar or identical to that of the example configuration of FIGS. 2A-D, the connector can support a plurality of terminals for electrically connecting the control unit 200 to the stimulation electrodes 170 and the recording electrodes 180. Certain terminals in the connector can be electrically connected to the stimulation electrodes 170 by wires or leads that are embedded within the plastic housing material (e.g., via insert molding). Embedding the leads in this manner helps maintain adequate spacing between the conductors, which avoids the potential for shorts in the circuitry.

Other terminals in the connector can be electrically connected to the recording electrodes 180 by wires or leads 184 that are partially embedded within the plastic housing material (e.g., via insert molding) and pass through the housing 176, extending to the recording electrodes 180. Through this configuration, all of the necessary electrical connections to the stimulation and recording electrodes 170, 180 are made when the control unit 200 is installed on the neurostimulator 110.

Referring to FIGS. 4C-D, the neurostimulator 110 is assembled by connecting the first and second portions 132, 134 of the upper portion 130 with the adjustment band 136. The upper and lower portions 130, 150 are interconnected by two adjustment bands 122 that interconnect their respective tab portions 144, 156. This completes the assembly of the neurostimulator 110, placing it in a condition to be worn by the subject in the manner illustrated in FIGS. 3A-B.

To use the neurostimulator 110, the brace 120 is simply unfolded and the control unit 200 is connected to the housing 176 via the connectors. The hook and loop fasteners 140, 142 and 152, 154 are disconnected, the brace 120 wrapped around the appropriate anatomy of the subject. In FIGS. 3A-B, the upper portion 130 is wrapped around the lower leg/ankle 112 of the subject, and the lower portion 150 is wrapped around the foot 114 of the subject. The hook and loop fasteners 140, 142 and 152, 154 are re-connected to attach neurostimulator 110 to the subject. Conveniently, where the neurostimulator 110 is configured for stimulating the tibial nerve in the position illustrated in FIGS. 3A-B, the upper portion 130 of the brace 120 can include visual alignment cues 210, such as holes in the brace, that become aligned with the medial malleolus of the ankle when the stimulating electrodes 170 are properly positioned.

Additional Brace Implementation

FIGS. 10A-B illustrate a brace implementation of the system that is similar to the brace of FIGS. 3A-4D. In this implementation, the electronic medical device 500 comprises a neurostimulator 510 that includes a brace 520 that supports the neurostimulator components on the subject in a manner similar in general to that illustrated in FIGS. 3A-B.

The brace 520 implementation of the neurostimulator 510 is advantageous in that it is versatile in its ability to position the stimulating electrodes and recording electrodes at different locations on the subject. For example, stimulating electrodes can be positioned on the upper portion 530 of the brace 520 wrapped around the ankle, and recording electrodes can be positioned on the lower portion 550 of the brace wrapped around the foot. This can be especially advantageous for closed-loop neurostimulation of the tibial nerve. In this implementation, stimulating electrodes on the upper portion 530 can be located between the medial malleolus and the Achilles tendon to provide electrical stimulation to the tibial nerve. Recording electrodes on the lower portion 550 can be located on the bottom of the subject's foot, near the flexor muscles (abductor hallucis and the flexor hallucis brevis) for the big toe and can record the EMG signals that result from recruitment of the tibial nerve's motor fibers.

The construction of the brace 520 is illustrated in FIG. 10B. The brace 520 is a single piece garment in configured so that heel ends 552 of the lower portion 550 can be interconnected, e.g., by stitching, to define a portion for receiving a heel of the subject. The upper portion 530 of the brace 520 includes two straps 540 and 544, each of which are two-piece structures that are connectable via a hook and loop fastener. More specifically, ankle strap 540 includes pieces 540a and 540b, one of which includes a hook portion of the fastener and the other of which includes the loop portion of the fastener. 142, which are positioned opposite each other along an upper extent of the upper portion. Foot strap 544 includes pieces 544a and 544b, one of which includes a hook portion of the fastener and the other of which includes the loop portion of the fastener.

The neurostimulator 510 includes a several of components that are secured or otherwise supported on the brace 520. The securement of these components can be achieved in a variety of manners, such as by adhesives, stitching, mechanical fastening, hook and loop fasteners, or a combination thereof. FIG. 10A illustrates the neurostimulator 510 in a partially assembled condition, with the electronic components of the neurostimulator mounted on the brace 520 prior to the heel ends 552 being interconnected. This construction is advantageous because it allows the electronic components of the neurostimulator 510 to be assembled onto brace 520 while the upper and lower portions 530, 550 lie flat. The lying flat illustration of FIG. 10A is for purposes of simplicity as it allows the upper and lower portions 530, 550 to be illustrated lying flat.

The neurostimulator 510 includes stimulation electrodes 570. In this example implementation, the stimulation electrodes 570 are arranged in pairs on the lower portion 550 near the heel ends 552. In other configurations, the stimulation electrodes could be arranged in one or more arrays including a plurality (e.g., more than two) of electrodes. The example configuration of FIG. 10A is ambidextrous, so one pair of electrodes 570 is for a right foot use, and the other pair of electrodes is for a left foot use.

The number of stimulation electrodes 570 (i.e., 2 or more), the size or area covered by the stimulation electrodes 570 and/or the electrode arrays, the electrode density (i.e., number of electrodes per unit area) of the arrays, and the distribution or pattern of electrodes within an array all can vary depending on the intended application of the neurostimulator 510. The location/position of the electrodes 570 on the brace 520 are by way of example only and are by no means limiting.

The stimulation electrodes 570 can be dry electrodes, in which case the neurostimulator 510 can include one or more removable/replaceable stimulation gel pads shaped and sized to coincide with and cover the stimulation electrodes 570. In use, the gel pads 174 facilitate a strong, reliable electrical connection between the stimulation electrodes 570 and the subject's skin.

The neurostimulator 510 also includes recording electrodes 580. In this example implementation, the recording electrodes 580 are elongated arranged spaced and parallel to each other on the upper portion 530 of the brace 520 at a location spaced from the stimulation electrodes 570. The spacing between the stimulation electrodes 570 and the recording electrodes 580 can be important, as it can be necessary to provide adequate distance between the electrodes so that electrical stimulation signals can be separated or distinguished from responses (e.g., neurological, muscular, neuromuscular, etc.) to those electrical stimulation signals. This facilitates utilizing responses to stimulation sensed by the recording electrodes 580 as feedback in a closed-loop stimulation control scheme which, again, is described in detail below.

In the configuration illustrated in FIG. 10A, the recording electrodes 580 are elongated, parallel, and positioned to be located on the bottom of the subject's foot. Because the bottom of the foot is curved, i.e., arched, and because good electrode contact is necessary to record EMG responses, the brace 520, electrodes 580, or both the brace and electrodes are configured so that the electrodes 580 are pressed against the foot bottom when the brace 520 is worn. This can be done in a variety of manners, such as by forming the electrode to have an upward facing convex surface configured to contact the foot arch, by padding the brace beneath the electrodes, or by installing a mechanical component, such as a leaf spring that biases the electrodes against the foot.

In the example configuration of FIG. 10A, like the stimulation electrodes 570, the recording electrodes 580 can also be dry electrodes. Because of this, the neurostimulator 510 can also include removable/replaceable recording gel pads shaped and sized to coincide with and cover the recording electrodes 580. In use, the gel pads facilitate a strong, reliable electrical connection between the recording electrodes 580 and the subject's skin.

Referring to FIG. 10A, the neurostimulator 510 also includes an electronic control unit ("controller") 600 that is operative to control the application of transcutaneous electrical nerve stimulation via the stimulating electrodes 570 and to receive stimulation feedback gathered by the recording electrodes 580. The control unit 600 is mounted on the upper portion 530 of the brace 520 on one of the straps 544b.

The neurostimulator 510 also includes electrical traces 590 that connect the controller 600 to the stimulating electrodes 570 and recording electrodes 580. The traces 590 and electrodes 570, 590 can be fixed to the brace 520 in a variety of manners, such as by adhesives, thermal bonding, or mechanical fastening. In one particular example, the traces 590 and/or electrodes 570, 580 can be applied to the brace 520 via a 3D printing technique in which they are formed in situ directly on the brace. In another particular example, the traces 590 can be applied to the brace 520 by first printing the traces onto a polymeric film such as PET, and then thermally imprinting the PET film onto the garment, with the traces facing the garment.

One example configuration of the controller 600 is illustrated in FIGS. 11A-14C. The controller 600 has a two-piece construction in which a base 610 is fixedly connected to the brace 520 and a control module 620 is removable connected to the base. The control module 620 includes the electronic components of the controller 600, and the base 610 facilitates an electrical connection to the electrodes 570, 580 on the brace 520. The connection between the control module 620 and the base 610 is provided via an electrical connector that supports the control module in the base and simultaneously provides electrical connections between the control module and the electrodes 570, 580 via the traces 590.

Advantageously, the plug-in configuration of the control module 620 allows it to be removed and connected to a power source for recharging or to a computer for programming. Also, configuring the controller 600 to be detachable/removable allows the controller to be utilized with other neurostimulator configurations and also allows the brace 520 and the components remaining on the brace (e.g., the electrodes, etc.) to be replaced when worn out, expired, or otherwise due for replacement.

Control Unit Configuration

The control units 70, 200 of the example configurations of the neurostimulator 10, 110 of FIGS. 1A-4D can have a variety of configurations. An example configuration for the control units 70, 110 is shown in FIG. 5. Referring to FIG. 5, the control unit 70, 200 includes a microcontroller 220 powered by a primary or rechargeable battery 222 via a battery protection and charging circuit 224. The circuit 224 offers battery protection typical for a medical device, such as over-current and over-voltage protection, under-voltage protection, and a charging controller. An external cable or charging cradle 226 charges the battery 222 via the circuit 224. Alternatively, the battery 222 can be charged wirelessly, e.g., via a wireless charging cradle. A pushbutton 228 cycles on/off power to the control unit 70, 200.

The battery protection and charging circuit 224 also marshals power to a high voltage power supply circuit 230, a digital power supply circuit 232, and an analog power supply circuit 234. The high-voltage power supply circuit 230 is used to provide a stimulation compliance voltage to the output stage's current sources and sinks. Since this device is a transcutaneous stimulator, it can require a compliance voltage in the range of about 40-200 V or more in order to provide the necessary current to stimulate the tibial nerve. For this embodiment, a compliance voltage of 120 volts is used for the compliance voltage.

A radio controller 240, such as a Bluetooth® or Zigbee® radio controller, provides a communication input to the microcontroller 220 for functions such as programming the control unit 70, 200, uploading/downloading data, and monitoring/controlling the neurostimulator 10, 110 during use. The radio controller 240 could, for example, pair the microcontroller to an enabled device, such as a smartphone, tablet, or computer, executing software that enables the user to monitor or otherwise control the operation of the neurostimulator 10, 110. The microcontroller 220 controls the operation of indicators 242, such as LEDs, that indicate the state or condition of the control unit 70, 210. The microcontroller 220 can control an accelerometer 244, which can provide input to determine whether the neurostimulator 10, 110, and thus the subject, is moving or at rest.

The microcontroller 220 is responsible for controlling the stimulation output, measuring the electrode impedance, and processing the EMG response. The microcontroller 220 runs software for performing these functions, including decision-making algorithms to allow the device to provide the desired therapy. The microcontroller 220 controls the operation of an amplitude control circuit 250, a timing control circuit 252, and a digital-to-analog converter (DAC) 254. By "circuit," it is meant that these functions can be implemented in any desired manner, e.g., through discrete components, integrated circuits, or a combination thereof. The amplitude control circuit 250, timing control circuit 252, and DAC 254 drive a stimulator output stage 260, which provides stimulator output signals (e.g., pulse-width-modulated "PWM" output signals) to one or more analog output switches 262. The output switch(es) 262 are operatively connected to a port 280 comprising a plurality of terminals (E1-E8 in FIG. 5) that facilitates connecting the control unit 70, 200 to the stimulator and recording electrodes, for example, via the leads 66, 184 (see, FIGS. 2A and 4B, respectively). Through this connection via the leads 66, 184, the stimulator output stage 260 can be operatively connected to the stimulator electrodes 50, 170.

The microcontroller 220 receives electrode impedance values via an impedance measurement circuit 264 that is operatively connected to the stimulator output stage 260. The microcontroller 220 also receives electrode feedback values (e.g., F-wave and M-wave values) via an analog front end 270 that is operatively connected to one or more analog input switches 272. The input switch(es) 272 are also operatively connected to the terminals/port 280 and can thereby receive feedback from the recording electrodes 60, 180 that facilitates connecting the control unit 70, 200 to the stimulator and recording electrodes, for example, via the leads 66 (see, FIG. 2A) or 184 (see, FIG. 4B).

The impedance measurement circuit 264 allows for measuring the impedance of the electrodes. It is important to measure the impedance often, in case one or more of the electrodes begins to lift from the skin. There are two potential hazards related to electrode lifting that should be mitigated. First, if an electrode is partially lifted from the skin, the surface area of the electrode that is in contact with the skin is reduced and the current density of the stimulation current is increased, which can be unsafe. Second, if an active electrode is completely lifted from the skin, a brief but large amount of energy can be delivered to the tissue when the electrode makes contact with the skin, which can result in pain.

Electrode impedances measured via the impedance measurement circuit 264 can also be used as an additional input for a closed-loop stimulation optimization algorithm.

The stimulator output stage 260 provides the current to the stimulating electrodes via the output switch 262. Each channel of the output stage includes a current source and current sink, which allows each channel to provide either a positive or negative current to the tissue through the corresponding stimulation electrode(s) 50, 170. In this configuration, each current source and sink can have independently programmable amplitude control 250 and timing control 252, which provides the capability to "steer" the current applied via the stimulation electrodes 50, 170, as described below. The programmable range can vary depending on the application, and is selected to be capable of achieving the desired nerve recruitment. In an example configuration, the current sources can have a programmable range from zero to +20 milliamperes (mA), and the current sinks can have a programmable range from zero to –20 mA.

As shown in FIG. 5, the analog output switches 262 and input switches 272 can both be operatively connected to each of the terminals E1-E8. Through operation of the switches 262, 272 as commanded by the microcontroller 220, the identity or role of the terminals, i.e., output terminal or input/feedback terminal, can be actively identified. This allows the microcontroller 220 to selectively identify, activate, and deactivate electrodes in a desired pattern, order, combination, etc., according to the particular therapy regimen being applied. This also allows the therapy to be tailored, for example, in response to signals received from the recording electrodes.

Control Overview

According to one example implementation, the neurostimulator 10, 100 described above can control the application of stimulation therapy according to two general phases: nerve localization and stimulation delivery. These two phases work synergistically to provide the functionality set forth in the following paragraphs.

During the nerve localization phase, the target peripheral nerve structure, e.g., the tibial nerve, is localized when the neurostimulator 10, 100 is donned and activated. In the nerve localization phase, the neurostimulator 10, 100 implements a process in which the following functions are performed:

Ramping up stimulation energy across various electrode patterns.

Monitoring EMG response after each stimulation pulse.

Determining the stimulation parameters that optimally activate the target peripheral nerve.

During the stimulation delivery phase, electrical stimulation is delivered to the target peripheral nerve structure using the stimulation parameters determined during the nerve localization phase. In the stimulation delivery phase, the neurostimulator 10, 100 implements a process in which the following functions are performed:

Deliver stimulation pulses to the target peripheral nerve.

Continuously optimize the delivery of stimulation pulses, which includes:

Monitoring EMG response after each stimulation pulse.

Monitoring electrode impedance.

Adjusting stimulation parameters to optimize recruitment of the tibial nerve.

Automatically stopping stimulation at the end of the therapy session.

The nerve localization and stimulation delivery phases are described in more detail in the following sections.

Nerve Localization

In a configuration of the system that implements a stimulation electrodes 50, 170 in a single pair, i.e., not in an array 52, 172, the stimulation parameters that can be adjusted in the nerve localization phase include signal amplitude, modulation patterns, polarity, frequency, duration, etc. In a configuration of the system that implements stimulation electrode arrays 52, 172, the stimulation parameters can additionally include patterns of stimulation electrodes 50, 170 selected from the arrays. The following description covers the illustrated implementations, i.e., those that include electrode arrays 52, 172.

In practice, the control unit 110 can be programmed with a set of electrode patterns that identify which stimulation electrode 50, 170 in an electrode array 52, 172 are active, and also the polarity or type, i.e., anode (+) or cathode (–) assigned to the electrode. FIG. 6 illustrates an example configuration for an electrode array 52, 172 and a chart illustrating an example set of electrode patterns. In the example illustrated in FIG. 6, the electrode array 52, 172 has eight electrodes 50, 170, identified at E1-E8, and the chart identifies ten different electrode patterns (patterns 1-10) for the electrode array. For each electrode pattern, each electrode is identified as being a cathode (C), anode (A), or inactive (blank). Thus, for example, in pattern 3, electrodes E1 and E2 are cathodes, electrodes E5 and E6 are anodes, and electrodes E3, E4, E7, and E8 are inactive. While there are a large number of patterns that are possible with an eight-electrode array, the patterns can effectively be narrowed down to a shorter list, such as the illustrated 10 patterns or more, depending on the nerve under recruitment.

The neurostimulator 10, 110 can be configured to perform a nerve localization routine to determine which of the electrode patterns should be utilized on a subject. In the example configuration of FIG. 6, the electrode array 52, 172 can be specifically designed, i.e., shaped and electrodes positioned, to stimulate the tibial nerve in the region between the medial malleolus and the Achilles tendon. The electrode array 52, 172 can be configured to perform stimulation on this or other regions where peripheral nerve stimulation is desired.

In the example configuration of FIG. 6, the electrode array 52, 172 is curved to allow the medial malleolus to be used as a placement guide. Also, the array can be symmetrical so that it can be placed on either ankle. The electrode arrangement within the array must be configured to capture the tibial nerve, meaning that the nerve must pass below or between at least one pair of electrodes. If the tibial nerve passes outside the extents of the array, activation of the tibial nerve requires much higher stimulation energies, or it may not be possible to activate the tibial nerve at all.

The implementation of stimulation electrode arrays 52, 172, as opposed to a single pair of electrodes, can be used to create an optimized stimulation field for recruiting the target (e.g., tibial) nerve. In order to optimize the stimulation field, the stimulation current can be steered using multiple electrodes. For example, electrode pattern 8 assigns electrodes E3 and E4 as anodes and electrodes E7 and E8 as cathodes. Viewing the arrangement of these electrodes 50, 170 on the array 52, 172, it can be seen that the use of this electrode pattern could be effective on a nerve path that passes directly adjacent or between these electrode pairs.

By selecting the appropriate stimulation electrodes 50, 170 from the stimulation electrode arrays 52, 172, and varying the amplitude and polarity of the current applied via the selected electrodes, the electric field applied to the subject can be shaped so that the current is steered to the target nerves. By shaping the field, the neurostimulator 10, 100 can automatically adjust to day-to-day donning and placement variability for a given subject. Current steering also allows the neurostimulator 10, 100 to work across a subject population with wide anatomical variation, for example providing a shallow field for subjects with nerves that are superficial to the skin, or a penetrating field for subjects with nerves that are deep. In the illustrated example configurations, the stimulation electrode arrays 52, 152 include six electrodes. Any number of stimulation electrodes greater than one can be used. In general, the "field steering" capability of the neurostimulator 10, 100 increases with the number of stimulating electrodes 50, 170 that are included.

Because there will be session-to-session variability in the location of the stimulating electrode array 52, 172 due to the don/doff process, as well as variability in skin/tissue impedance, providing open-loop stimulation applying rigid preprogrammed stimulation parameters could be disadvantageous, often providing too little or too much stimulation energy to recruit the nerve. Advantageously, the nerve localization algorithm is executed at the beginning of each therapy session to determine which of the preprogrammed electrode patterns will be most effective.

FIG. 7 illustrates a flowchart showing the method or process 300 implemented by the nerve localization algorithm. The steps in the process 300 are not meant to be exclusive, i.e., other steps can be included. Nor is the process 300 intended to be strictly followed in terms of the order shown in FIG. 7 or described herein. The process 300 illustrates steps, perhaps a minimum, necessary to localize the peripheral nerve that is to be stimulated.

It should be noted here that, the process 300 is a closed-loop algorithm that utilizes feedback recorded via the recording electrodes 60, 180 to make determinations and/or adjust settings. As such, the process 300 relies on utilization of the feedback to determine which of the electrode patterns effectively achieves nerve recruitment. Specifically, the process 300 relies on feedback from the recording electrodes 60, 180 to provide indication of EMG response feedback. Alternatively, the process 300 can rely on accelerometers to provide MMG response feedback.

Referring to FIG. 7, the process 300 begins at step 302, where an impedance measurement is performed in order to determine which, if any, of the electrodes E1-E8 have open or prohibitively high impedance. This step 302 can be considered an integrity check for the electrodes 50, 170 in the array 52, 172 to determine if any of the electrodes in the array are not sufficiently contacted with the skin. If any of the electrodes in the array are determined to be performing in a substandard manner, indicated by displaying an open (infinitely high) or sufficiently high impedance, those electrodes and the electrode patterns that utilize those electrodes can be eliminated from use.

For example, in the example of FIG. 6, it can be seen from row 2 that electrode E6 has high impedance. In this instance, electrode patterns 3, 6, 7, and 9 are eliminated form use in the current therapy session. Alternatively, the algorithm could instruct the control unit to provide some indication to the user, such as an alarm or display, to re-position or adjust the electrodes to see if contact can be improved.

To avoid interfering with stimulation and EMG measurement, the integrity check at step 302 can be completed in a short amount of time, such as 25 milliseconds or less. Also, the impedance measurement can be conducted so as to cause little or no sensation in the subject's skin. Therefore, the excitation current for performing the integrity check should be low-amplitude, such as 1 mA or less. For the integrity check 302, the impedance value at each electrode is not critical. Instead, determining whether the impedance is below a certain threshold is adequate.

Additionally, conditions other than high or low impedance can be determined in this integrity check. For example, indicators such as dry/wet contact checks, whole/brittle/fractured contact checks, contact surface area checks, and contact reflectance checks can be made during the connectivity evaluation. Sensors, such as don/doff, stretch, strain, bending or contact sensors (via electrical, optical or mechanical means) can also be used for conducting the connectivity evaluation. These sensors could also be incorporated into a buckle, clasp, snap, hook/eye or zipper feature.

Once the integrity check is performed, the process 300 proceeds to step 304 where the first electrode pattern (that hasn't been eliminated by the integrity check) is loaded. The process 300 then proceeds to step 306 where the neurostimulator 10, 110 generates stimulation pulse(s) using the electrode pattern loaded in step 304. The process 300 proceeds next to step 310, where a determination is made as to whether the stimulation pulses generated at step 306 elicited an EMG response, i.e., feedback measured via the recording electrodes. Step 310 can additionally or alternatively determine whether there is a MMG response where the feedback devices include accelerometer(s).

If, at step 310, EMG (or MMG) is not detected, the process 300 reverts to step 314, where a new electrode pattern is loaded. The process 300 then proceeds to step 306, as described above. If, at step 310, EMG (or MMG) is detected, the process 300 proceeds to step 312, where the electrode pattern is added according to pattern selection rules. The process 300 then proceeds to step 316, where a determination is made as to whether the current electrode pattern is the last electrode pattern in the list.

The pattern selection rules at step 312 for adding an electrode pattern can be defined to prioritize electrode patterns identified as being the best suited to recruit the target nerves. These pattern selection rules may be implemented as follows:

If one pattern is significantly better than the others (e.g., as determined from the EMG data, see below), that pattern should be used as the primary pattern moving forward.

If two or three patterns are roughly equivalent, any one of the patterns can be used as the primary pattern. Moving forward, this pattern can be switched to other ones if the nerve recruitment displayed by the current primary pattern begins to diminish.

If the nerve recruitment for a particular pattern begins to diminish and increasing the stimulation parameters does not fix the problem, similar patterns can be re-introduced to the algorithm.

If, at step 316, it is determined that the current electrode pattern is not the last pattern in the list, the process 300 reverts to step 314, where a new electrode pattern is loaded. The process 300 then proceeds to step 306, as described above. If, at step 316, it is determined that the current electrode pattern is the last pattern in the list, this indicates that the pattern list is complete. The process 300 proceeds to step 320 where the stimulation parameters for the electrode patterns in the pattern list are optimized. At step 320, the stimulation parameters (e.g., frequency, amplitude, pattern, duration, etc.) are updated to optimize the nerve recruitment for each pattern. The process 300 then reverts back to the initial step at 302 and proceeds as described above. If the recruitment for a given electrode pattern improves, the stimulation parameters are kept. If not, they revert back to previous values. This process repeats itself until the pattern list is filled with electrode patterns optimized for nerve recruitment.

From the above, it will be appreciated that the nerve localization process 300 determines which of the electrode patterns to utilize and which to discard for any given stimulation therapy session, and then optimizes the stimulation parameters for the utilized patterns. The execution of this process 300 is fast. During execution, the neurostimulator 10, 110 applies stimulation therapy pulses via the stimulating electrodes 50, 170 and monitors for EMG responses via the recording electrodes 60, 180 after each pulse.

The analog front end circuit 270 can replace traditional EMG measurement circuitry such as a filter, amplifier, rectifier, and/or integrator. The control unit 110 utilizes the analog front-end circuit 270 to sample the recording electrodes at a predetermined sample rate, such as 1,000-8,000 samples per second or more, for example, up to 20,000 samples per second. The EMG sampling window will begin after the stimulation pulse is finished, and the window will last for a predetermined brief period, such as 8-90 milliseconds. The resulting EMG data, comprised of M-wave or F-wave or both, can be analyzed using time or frequency domain control processing that clearly shows if EMG is present.

To execute the process 300 of FIG. 7, the neurostimulator 10, 110 monitors for electromyogram (EMG) signals via the recording electrodes 60, 180 in response to stimulation applied via the stimulation electrodes 50, 170. FIG. 8 illustrates examples of the EMG responses that can be recorded, which include: No EMG Response, F-wave Response, M-wave Response, and M and F-wave Response. In the example where no EMG response is recorded, the stimulation pulse artifact can be seen on the left, with no response following. In the example where an M-wave response is recorded, the stimulation pulse artifact can be seen on the left, followed by the M-wave at about 6 to 10 ms post-stimulation. In the example where an F-wave response is recorded, the stimulation pulse artifact can be seen on the left, followed by the F-wave responses at about 50 to 55 ms post-stimulation. In the example where both an M-wave and F-wave responses are recorded, the stimulation pulse artifact can be seen on the left, followed by the M-wave and F-wave at 6 to 10 ms and about 50 to 55 ms post-stimulation, respectively. These response times could change slightly, depending on a variety of factors, such as the hydration and/or salinity of the subject tissue, the arrangement and spacing of the electrodes, and the characteristics of the stimulation signals.

For each of the four recorded response scenarios, FIG. 8 also illustrates a corresponding Fast Fourier Transform (FFT) results for the raw post-artifact signal. The FFT results are calculated by the microcontroller 220 and are used in the process 300 to determine whether an EMG response is present (see, step 310 in FIG. 7). The FFT results shown in FIG. 8 are just one example method that can be implemented in the process 300 to evaluate the F-wave and M-wave responses. Those skilled in the art will appreciate that alternative time and frequency domain methods can also be implemented.

Stimulation Delivery

The neurostimulator 10, 110 can apply stimulation therapy using an open-loop control scheme, a closed-loop control scheme, or a combination of open-loop and closed-loop control schemes, depending on the control algorithm programmed into the microcontroller 220. For open-loop control, the control units 70, 200 can apply electrical stimulation via the stimulation electrodes 50, 170 according to settings (frequency, amplitude, pattern, duration, etc.) without regard to any feedback measured via the recording electrodes 60, 180. This is not to say that feedback is not measured, just that, in an open-loop control scheme, the feedback is not used to inform or control the algorithm executed by the microcontroller 220 to control the application of stimulation therapy. In a closed-loop control scheme, the neurostimulator 10, 110 implements a control algorithm in which feedback from the recording electrodes 60, 180 informs and helps control the application of stimulation therapy.

FIG. 9 illustrates by way of example a process 400 by which the neurostimulator 10, 110 controls the application of electrical nerve stimulation using the electrode pattern(s)

identified by the nerve localization process 300 of FIG. 7. The stimulation control process 400 can employ both open-loop and closed-loop control, with closed-loop steps or portions of the process being illustrated in solid lines and open-loop steps or portions being illustrated in dashed lines. Ideally, the process 400 will proceed with closed-loop control, as it is able to utilize feedback to optimize the application of stimulation therapy.

The process 400 begins at step 402, where the impedances of the recording electrodes 60, 180 are checked. If, at step 404, it is determined that the recording electrode impedances are too high (e.g., resulting in unavailable or unreliable feedback), the process 400 then shifts to open-loop mode (see dashed lines) and proceeds to step 412, where a gap is implemented. The purpose of gap 412 is to assist in maintaining a constant stimulation period, meaning that the duration of gap 412 should be equal to the duration of closed-loop step 406. After completing gap 412, the process 400 proceeds to step 414, where the stimulation electrode impedances are checked.

At step 404, if the impedances of the recording electrodes are acceptable, the process 400 remains in closed-loop mode and proceeds to step 406, where samples are obtained via the recording electrodes to check for significant noise or voluntary EMG responses. At step 410, if excessive noise or voluntary EMG are present, the feedback is considered unreliable and the process 400 shifts to open-loop mode and proceeds to step 414. At step 410, if significant noise or voluntary EMG is not present, the feedback is considered reliable and the process 400 remains in closed-loop mode and proceeds to step 414.

At step 414, regardless of whether the process is in open-loop mode or closed-loop mode, the impedances of the stimulation electrodes 50, 170 are checked. At step 416, if the stimulation electrode impedances are acceptable, the process 400 proceeds to step 420 and the neurostimulator 10, 110 generates stimulation pulses, which are applied via the stimulation electrodes. In a configuration implementing electrode arrays, the stimulation pulses are applied using the optimal electrode pattern, as determined by the nerve localization process 300 (see FIG. 7). If, at step 416, the stimulation electrode impedances are too high, the process 400 proceeds to step 420 and the neurostimulator 10, 110 generates stimulation pulses that are applied via the stimulation electrodes using an alternative electrode pattern selected from the pattern list determined by the nerve localization process 300. In a configuration implementing a single pair of electrodes, an unacceptable impedance measurement can result in a command to the user to adjust the positioning of the stimulation electrodes until an acceptable impedance is measured. In either case, once acceptable stimulation electrode contact has been established, the process 400 proceeds to step 424.

At step 424, the process 400 implements a pre-recording delay to allow time for the applied electrical stimulation to elicit an EMG response. As discussed above, these delays can be relatively short, so the delay at step 424 can, likewise, be short, e.g., 5 ms or less. If the process 400 is in open loop mode, it proceeds to step 432, where a further delay is implemented. This delay 432 should match the duration of closed-loop steps 426 and 430 so that a constant stimulation period is maintained. If the process 400 is in closed-loop mode, it proceeds to step 426 and checks for feedback via the recording electrodes 60, 180. The process 400 then proceeds to step 430, where any detected EMG feedback signals are recorded and analyzed. This time delay can be implemented as an actual delay, i.e., a waiting period between stimulation and recording, or by recording continually and ignoring a portion of the recording during and after stimulation.

At this point, regardless of whether the process 400 is in open-loop mode (step 432) or closed-loop mode (step 430), the process proceeds to step 434, where a determination of whether the number of stimulation pulses applied in the current therapy session has reached a predetermined number (N). If the predetermined number (N) of pulses have not yet been applied, the process proceeds to step 436, the stimulation amplitude is maintained at the current level, and the process 400 reverts back to step 402, where the impedance of the recording electrodes is checked and the process 400 repeats. If, at step 434, the predetermined number (N) of pulses has been reached, the process 400 proceeds to step 440.

At step 440, if the process 400 in open-loop mode, the process proceeds to step 442, the stimulation amplitude is maintained at the current level, and the process 400 reverts back to step 402, where the impedance of the recording electrodes is checked and the process 400 repeats. At step 440, if the process 400 is not in open-loop mode (i.e., is in closed-loop mode), the process proceeds to step 444, where a determination is made as to whether the EMG recorded at step 430 is below a predetermined window, i.e., below a predetermined range of acceptable EMG values. If the EMG is below the predetermined window, the process 400 proceeds to step 446, where the stimulation output (amplitude, pulsewidth, etc.) is increased for the next pulse, if permitted. The process 400 then reverts back to step 402, where the impedance of the recording electrodes is checked and the process 400 repeats with the increased stimulation output.

If, at step 444, the EMG is not below the window, the process 400 proceeds to step 450 where a determination is made as to whether the EMG is above the predetermined window. If the EMG is above the predetermined window, the process 400 proceeds to step 452, where the stimulation output is decreased for the next pulse. The process 400 then reverts back to step 402, where the impedance of the recording electrodes is checked and the process 400 repeats with the decreased stimulation output. If, at step 450, the EMG is not above the predetermined window, the EMG is determined to be within the predetermined window and the process 400 proceeds to step 454, where the stimulation output is maintained at the current level for the next pulse. The process 400 then reverts back to step 402, where the impedance of the recording electrodes is checked and the process 400 repeats.

PTNS or Implanted Electrode Control Implementation

While the systems and methods of the invention have been described herein as being used with surface mounted, transcutaneous tibial nerve stimulation, it will be appreciated that the control implementations described herein can also be applied to percutaneous tibial nerve stimulation (PTNS). Traditional PTNS utilizes through-the-skin stimulating electrodes in an open loop configuration where stimulation is applied without active sensing and/or control. According to another example implementation of the invention, the system/neurostimulator described above can control the application of stimulation therapy where the stimulation electrodes are percutaneous (through-the-skin) PTNS electrodes as opposed to surface mounted transcutaneous electrodes. In doing so, the PTNS can be applied according to the same two general phases described previously, i.e., nerve localization and stimulation delivery. Furthermore, the recording electrodes for closed-loop feedback control may be mounted on the skin, as part of the wearable or as a standalone, or they may be percutaneous, or they may be fully implanted, either as part of the stimulation electrodes system or as a stand-alone unit.

In the case of implanted electrodes, nerve localization may not be necessary because the electrodes can be positioned precisely relative to the target nerve. Still, it is envisioned that the implanted electrodes could still be arranged in an array of electrodes, in which case localization through electrode selection could be desirable. In any matter, for implanted electrodes, during the nerve localization phase, the neurostimulator implements a process, identical to that described above in the transcutaneous implementation, in which the following functions are performed:

Ramping up stimulation energy across various electrode patterns.

Monitoring EMG response after each stimulation pulse.

Determining the stimulation parameters that optimally activate the target peripheral nerve.

Furthermore, the recording electrodes for closed-loop feedback control may be mounted on the skin, as part of the wearable or as a standalone, or they may be percutaneous, or they may be fully implanted, either as part of the stimulation electrodes system or as a stand-alone unit.

During the stimulation delivery phase, electrical stimulation is delivered to the target peripheral nerve structure using the stimulation parameters determined during the nerve localization phase. In the stimulation delivery phase, the neurostimulator implements a process in which the following functions are performed:

Deliver stimulation pulses to the target nerve, e.g., tibial nerve.

Continuously optimize the delivery of stimulation pulses, which includes:

Monitoring EMG response after each stimulation pulse.

Monitoring electrode impedance.

Adjusting either the electrode pattern (current-steering) or stimulation energy to optimize recruitment of the target nerve, e.g., tibial nerve.

Automatically stopping stimulation at the end of the therapy session.

The nerve localization and stimulation delivery phases implemented in the PTNS implementation can be similar or identical to those described in detail in the above sections with the headings "Nerve Localization"and "Stimulation Delivery."Of course, those skilled in the art will appreciate that certain modifications and/or accommodations might need to be made to account for the particulars that one would encounter with PTNS or implanted electrodes as opposed to surface mounted transcutaneous electrodes.

While aspects of this disclosure have been particularly shown and described with reference to the example aspects above, it will be understood by those of ordinary skill in the art that various additional aspects may be contemplated. A device or method incorporating any of the features described herein should be understood to fall under the scope of this disclosure as determined based upon the claims below and any equivalents thereof. Other aspects, objects, and advantages can be obtained from a study of the drawings, the disclosure, and the appended claims.

We claim:

1. A method for treating a medical condition by delivering electrical stimulation to a target peripheral nerve of a subject, comprising:

positioning a plurality of stimulation electrodes in a predetermined configuration proximate the target peripheral nerve;

positioning one or more recording electrodes remote from the stimulation electrodes at a location where electromyogram (EMG) responses to electrical stimulation of the target peripheral nerve can be detected;

localizing the target peripheral nerve by applying electrical stimulation pulses to the target peripheral nerve via the plurality of stimulation electrodes with different stimulation energies, monitoring via the recording electrodes the EMG responses elicited by each electrical stimulation pulse, and identifying pulse energies that elicit an acceptable activation of the target peripheral nerve;

in response to identifying pulse energies that elicit an acceptable activation of the target peripheral nerve, initially delivering stimulation to the target peripheral nerve by applying electrical stimulation pulses via the stimulation electrodes at the identified pulse energies that elicited the acceptable activation of the target peripheral nerve; and thereafter delivering electrical stimulation to the target peripheral nerve to treat the medical condition by controlling the delivery of stimulation to the target peripheral nerve using closed-loop control in which EMG responses to the electrical stimulation pulses are monitored via the recording electrodes and stimulation parameters are adjusted in response to the monitored EMG responses, and while electrical stimulation is being delivered to the target peripheral nerve under closed-loop control, performing an integrity check comprising applying, between stimulation pulses, a low-level current across the stimulation electrodes selected so as not to interfere with EMG measurements by the recording electrodes, and detecting a response to the low-level current via the stimulation electrodes to complete the integrity check.

2. The method recited in claim 1, wherein the stimulation parameters comprise at least one of an amplitude of the electrical stimulation pulses, a modulation pattern of the electrical stimulation pulses, the frequency of the electrical stimulation pulses, the duration of the electrical stimulation pulses, and the polarity of the stimulation electrodes.

3. The method recited in claim 1, wherein controlling the delivery of stimulation to the target peripheral nerve using closed-loop control comprises:

obtaining EMG measurements via the recording electrodes;

checking the EMG measurements for at least one of noise and voluntary EMG responses; and applying the electrical stimulation pulses under closed-loop control in response to determining an acceptable level of noise and/or the absence of voluntary EMG responses.

4. The method recited in claim 1, wherein controlling the delivery of stimulation to the target peripheral nerve using closed-loop control comprises:

applying the electrical stimulation pulse; implementing a time delay;

recording EMG responses via the recording electrodes after the time delay; and adjusting the stimulation parameters in response to the recorded EMG responses.

5. The method recited in claim 4, wherein the duration of the time delay is about 5 ms or less.

6. The method recited in claim 4, wherein adjusting the stimulation parameters in response to the recorded EMG responses under closed loop control comprises:

adjusting the stimulation parameters of subsequent stimulation pulses in response to the recorded EMG responses being outside a predetermined EMG window; and maintaining the stimulation parameters of subsequent stimulation pulses in response to the recorded EMG responses being within the predetermined EMG window.

7. The method recited in claim 4, wherein adjusting the stimulation parameters in response to the recorded EMG responses under closed loop control comprises:

increasing the output of subsequent stimulation pulses in response to the recorded EMG responses being below a predetermined EMG window;

decreasing the output of subsequent stimulation pulses in response to the recorded EMG responses being above the predetermined EMG window; and maintaining the output of subsequent stimulation pulses in response to the recorded EMG responses being within the predetermined EMG window.

8. The method recited in claim 1, further comprising:

detecting an unacceptable condition of the recording electrodes in response to failing to elicit an acceptable activation of the target peripheral nerve when localizing the target peripheral nerve during the localizing step; and in response to detecting the unacceptable condition of the recording electrodes, controlling the delivery of stimulation to the target peripheral nerve using open-loop control in which stimulation is delivered to the target peripheral nerve using stimulation parameters applied without regard to the monitored EMG responses.

9. The method recited in claim 8, wherein each application of an electrical stimulation pulse under open-loop control comprises:

applying the electrical stimulation pulse; and executing a time gap having a duration sufficient to maintain a stimulation period that is constant with a stimulation period of closed-loop control.

10. The method recited in claim 9, wherein the duration of the time gap is about 75 ms.

11. The method recited in claim 8, wherein the unacceptable condition of the recording electrodes comprises at least one of an unacceptable impedance measurement, an unacceptable noise measurement, or the detection of a voluntary EMG response.

12. The method recited in claim 1, wherein the nerve localization step comprises:

checking the sample measurements for at least one of noise and voluntary EMG responses;

controlling the delivery of stimulation to the target peripheral nerve using closed-loop control in response to determining an acceptable recording electrode impedance and an acceptable level of noise and/or the absence of voluntary EMG responses; and controlling the delivery of stimulation to the target peripheral nerve using open-loop control in response to determining an unacceptable recording electrode impedance, an unacceptable level of noise, or the presence of voluntary EMG responses.

13. The method recited in claim 1, wherein the plurality of stimulation electrodes comprises three or more stimulation electrodes, and wherein localizing the target peripheral nerve comprises applying electrical stimulation pulses to the target peripheral nerve via different combinations of the plurality of stimulation electrodes with different stimulation energies, monitoring via the recording electrodes the EMG responses elicited by each electrical stimulation pulse, and identifying both the stimulation electrode combinations and the pulse energies that elicit an acceptable activation of the target peripheral nerve.

14. The method recited in claim 13, wherein initially delivering stimulation to the target peripheral nerve comprises applying electrical stimulation pulses via the identified combinations of stimulation electrodes at the identified pulse energies that elicited the acceptable activation of the target peripheral nerve; and wherein delivering electrical stimulation to the target peripheral nerve to treat the medical condition by controlling the delivery of stimulation to the target peripheral nerve using closed-loop control comprises delivering electrical stimulation via the identified combinations of stimulation electrodes.

15. The method recited in claim 1, wherein stimulating the peripheral nerve comprises stimulating the tibial nerve, and wherein monitoring the EMG responses via the recording electrodes comprises recording EMG signals that result from recruitment of the tibial nerve's motor fibers.

16. The method recited in claim 15, wherein positioning a plurality of stimulation electrodes comprises positioning the plurality of stimulation electrodes at a location between the medial malleolus and the Achilles tendon, and wherein positioning one or more recording electrodes comprises positioning the one or more recording electrodes on the bottom of the subject's foot near the abductor hallucis and the flexor hallucis brevis.

17. The method recited in claim 1, wherein the medical condition comprises pelvic floor dysfunction.

18. The method recited in claim 1, wherein the medical condition comprises bladder dysfunction.

19. The method recited in claim 1, wherein the medical condition comprises urinary incontinence, which comprises at least one of urge incontinence, overactive bladder (OAB), mixed incontinence, and overflow incontinence.

20. The method recited in claim 1, wherein the medical condition comprises voiding dysfunction, which comprises at least one of urinary incontinence, urinary retention conditions, high urinary frequency, high frequency of voiding, low frequency of voiding, underactive bladder, symptoms of bladder/pelvic pressure/pain, detrusor hyperrflexia, and voiding disorders caused by nerve damage, including interstitial cystitis.

21. The method recited in claim 1, wherein the medical condition comprises bowel dysfunction.

22. The method recited in claim 1, wherein the medical condition comprises constipation, idiopathic constipation, fecal incontinence, problems with fecal movement, problems with fecal voiding, and problems with fecal containment.

23. The method recited in claim 1, wherein the medical condition comprises improving pelvic floor function bowel dysfunction.

24. The method recited in claim 1, wherein delivering electrical stimulation to the target peripheral nerve to treat the medical condition comprises stimulating the ulnar nerve and/or median nerve for pain management in carpal tunnel syndrome, hypertension management, and nerve conduction study/nerve injury diagnosis for median/ulnar nerve neuropathy.

25. The method recited in claim 1, wherein delivering electrical stimulation to the target peripheral nerve to treat the medical condition comprises stimulating the ulnar nerve and/or median nerve to treat carpal tunnel syndrome or hypertension.

26. The method recited in claim 1, wherein delivering electrical stimulation to the target peripheral nerve to treat the medical condition comprises stimulating the ulnar nerve and/or median nerve to perform a nerve conduction study or nerve injury diagnosis.

27. The method recited in claim 1, wherein delivering electrical stimulation to the target peripheral nerve to treat the medical condition comprises applying the electrical stimulation pulses to the peripheral nerve to enhance nerve regeneration after peripheral nerve injury.

28. The method recited in claim 1, wherein delivering electrical stimulation to the target peripheral nerve to treat the medical condition comprises applying the electrical stimulation pulses to the peripheral nerve to treat pelvic pain.

29. The method recited in claim 1, wherein delivering electrical stimulation to the target peripheral nerve to treat the medical condition comprises applying the electrical stimulation pulses to the peripheral nerve to treat peripheral neuropathy.

30. A system for treating a medical condition by applying electrical stimulation to a target peripheral nerve of a subject, comprising:

a plurality of electrical stimulation electrodes; one or more recording electrodes; and a control unit for controlling the operation of the stimulation electrodes and the recording electrodes according to the method of claim 1.

31. A controller for controlling the operation of a plurality of electrical stimulation electrodes and one or more recording electrodes to treat a medical condition by applying electrical stimulation to a target peripheral nerve of a subject according to the method of claim 1.

* * * * *